United States Patent
Lin et al.

(10) Patent No.: US 11,712,496 B2
(45) Date of Patent: Aug. 1, 2023

(54) MICROSPHERES CONTAINING DECELLULARIZED DONOR TISSUE AND THEIR USE IN FABRICATING POLYMERIC STRUCTURES

(71) Applicants: UNIVERSITY OF CINCINNATI, Cincinnati, OH (US); CHILDREN'S HOSPITAL MEDICAL CENTER, Cincinnati, OH (US)

(72) Inventors: Chia-Ying James Lin, Mason, OH (US); Stacey Gruber, Cincinnati, OH (US); Patrick W. Whitlock, Cincinnati, OH (US); Paulomi Ghosh, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 428 days.

(21) Appl. No.: 16/759,380

(22) PCT Filed: Oct. 26, 2018

(86) PCT No.: PCT/US2018/057751
§ 371 (c)(1),
(2) Date: Apr. 27, 2020

(87) PCT Pub. No.: WO2019/084432
PCT Pub. Date: May 2, 2019

(65) Prior Publication Data
US 2020/0289702 A1 Sep. 17, 2020

Related U.S. Application Data

(60) Provisional application No. 62/578,037, filed on Oct. 27, 2017.

(51) Int. Cl.
*A61L 27/18* (2006.01)
*B33Y 80/00* (2015.01)
(Continued)

(52) U.S. Cl.
CPC ........... *A61L 27/18* (2013.01); *A61L 27/3612* (2013.01); *A61L 27/3683* (2013.01);
(Continued)

(58) Field of Classification Search
CPC .. A61L 27/18; A61L 27/3612; A61L 27/3683; A61L 2430/06; A61L 2300/622;
(Continued)

(56) References Cited

U.S. PATENT DOCUMENTS

2012/0330423 A1 12/2012 Lin et al.
2015/0023911 A1 1/2015 Schilling et al.
(Continued)

FOREIGN PATENT DOCUMENTS

WO 2009092094 A1 7/2009

OTHER PUBLICATIONS

Vineet Gupta et al, Microsphere-based scaffolds encapsulating chondroitin sulfate or decellularized cartilage, J Biomater Appl, Sep. 2016, 31 (3); 328-343.

*Primary Examiner* — Nahida Sultana
(74) *Attorney, Agent, or Firm* — Dinsmore & Shohl LLP

(57) ABSTRACT

Decellularized matrix microspheres comprising a polymeric material and a donor tissue are provided. Also disclosed are structures containing a plurality of decellularized matrix microspheres incorporating a first polymer and a donor tissue; and a second polymer, wherein the decellularized matrix microspheres and the second polymer are in the form of a filament. Methods of treating a tissue injury employing
(Continued)

the matrix microspheres and structures described as well as their methods of manufacture are also provided.

10 Claims, 13 Drawing Sheets

Specification includes a Sequence Listing.

(51) Int. Cl.
| | |
|---|---|
| *B29C 64/118* | (2017.01) |
| *B33Y 70/10* | (2020.01) |
| *A61L 27/36* | (2006.01) |
| *B33Y 70/00* | (2020.01) |
| *B33Y 10/00* | (2015.01) |
| *B33Y 40/10* | (2020.01) |
| *B29K 67/00* | (2006.01) |
| *B29K 467/00* | (2006.01) |
| *B29L 31/00* | (2006.01) |

(52) U.S. Cl.
CPC ............ *B29C 64/118* (2017.08); *B33Y 70/00* (2014.12); *B33Y 70/10* (2020.01); *B33Y 80/00* (2014.12); *A61L 2430/06* (2013.01); *B29K 2067/00* (2013.01); *B29K 2467/046* (2013.01); *B29K 2489/00* (2013.01); *B29L 2031/7532* (2013.01); *B33Y 10/00* (2014.12); *B33Y 40/10* (2020.01)

(58) Field of Classification Search
CPC .... A61L 2300/624; A61L 27/38; A61L 27/54; B29C 64/118; B33Y 70/00; B33Y 70/10; B33Y 80/00; B33Y 10/00; B33Y 40/10; B29K 2067/00; B29K 2467/046; B29K 2489/00; B29L 2031/7532; A61K 35/28; A61K 35/32; A61K 38/18; A61P 19/08
See application file for complete search history.

(56) References Cited

U.S. PATENT DOCUMENTS

| | | | |
|---|---|---|---|
| 2017/0050052 A1* | 2/2017 | Burgett | B33Y 80/00 |
| 2017/0143831 A1* | 5/2017 | Varanasi | B33Y 10/00 |
| 2018/0085493 A1* | 3/2018 | Lee | A61L 27/3834 |
| 2020/0353673 A1* | 11/2020 | Mardjono | B29C 64/232 |

* cited by examiner (a)

(b)

MICROSPHERES CONTAINING DECELLULARIZED DONOR TISSUE AND THEIR USE IN FABRICATING POLYMERIC STRUCTURES

CROSS REFERENCE TO RELATED APPLICATIONS

This application is a § 371 U.S. National Stage Application of International Application No. PCT/US2018/057751 filed Oct. 26, 2018, and claims priority to U.S. Provisional Application No. 62/578,037 filed Oct. 27, 2017, the contents of which are incorporated herein by reference.

FIELD

The disclosure relates to microspheres containing decellularized donor tissue that remain functional after incorporation within a polymeric filament and their use in fabricating polymeric structures.

BACKGROUND

Articular cartilage is a highly complex connective tissue that covers the surface of the bones in synovial joints. Sophia Fox A J et al., The basic science of articular cartilage: structure, composition, and function, *Sports Health* 1: 461-8 (2009); and Temeno J S et al., Review: tissue engineering for regeneration of articular cartilage, *Biomaterials* 21: 431-40 (2000). Due to the limited proliferative capacity of chondrocytes and its avascular nature, injury to the osteochondral tissue can lead to progressive degradation—eventually to osteoarthritis and significant disability.

While current treatment options such as micro-fracture, autologous chondrocyte implantation and osteochondral autologous transfer improve the quality of life of some patients, they are not capable of regenerating functional cartilage akin to native tissue and are often highly case dependent. Moreover, the end product is fibrocartilage that is mechanically inferior to the hyaline cartilage. Gudas R, et al., A prospective randomized clinical study of mosaic osteochondral autologous transplantation versus microfracture for the treatment of osteochondral defects in the knee joint in young athletes, *Arthroscopy* 21: 1066-75 (2005); Xing L et al., Microfracture combined with osteochondral paste implantation was more effective than microfracture alone for full-thickness cartilage repair, *Knee Surg. Sports Traumatol. Arthrosc.* 21: 1770-6 (2013); Kok A C et al., No effect of hole geometry in micro-fracture for talar osteochondral defects, *Clin. Orthop. Relat. Res.* 471: 3653-62 (2013); Solheim E et al., Osteochondral autografting (mosaicplasty) in articular cartilage defects in the knee: results at 5 to 9 years, *Knee* 17: 84-87 (2010); Bartlett W et al., Autologous chondrocyte implantation versus matrix-induced autologous chondrocyte implantation for osteochondral defects of the knee: a prospective, randomised study, *J. Bone Joint Surg. Br.* 87: 640-645 (2005); Goyal D et al., Evidence-based status of microfracture technique: a systematic review of level I and II studies, *Arthroscopy* 29: 1579-88 (2013); Basad E et al., Matrix-induced autologous chondrocyte implantation versus microfracture in the treatment of cartilage defects of the knee: a 2-year randomized study, *Knee Surg. Sports Traumatol. Arthrosc.* 18: 519-27 (2010); and Zhang L et al., The role of tissue engineering in articular cartilage repair and regeneration, *Crit. Rev. Biomed. Eng.* 37: 1-57 (2009).

Currently there is no treatment for the restoration of large osteochondral injuries (OCI) that exceed the indications for micro-fracture, autologous chondrocyte implantation (ACI), and autologous osteochondral transfer (OAT) or (OAT) mosaicplasty. Furthermore, treatment with each of these methods have well-described limitations and benefits. Similarly, the formation of a stable bone-peri-articular cartilage interface able to support prolonged maintenance of healthy OC tissue and withstand joint forces in vivo represents a significant barrier to current tissue-engineered approaches to the repair of large OCI.

Therefore, treatment of osteochondral injuries, particularly >2.5 $cm^2$ in pediatric and adolescent patients, remains a major clinical challenge. Farr J et al., Clinical cartilage restoration: evolution and overview, *Clin. Orthop. Relat. Res.* 469: 2696-705 (2011); and Seo S J et al., Strategies for osteochondral repair: focus on scaffolds, *J. Tissue Eng.* 5: 1-14 (2014).

To overcome the limitations of current repair strategies, recent efforts have focused on producing three-dimensional (3D) constructs that can promote cell migration and cartilage regeneration by providing an instructive microenvironment to the progenitor cells. Id. and Bhattacharjee M et al., Role of chondroitin sulphate tethered silk scaffold in cartilaginous disc tissue regeneration, *Biomed. Mater.* 11: 025014 (2016); Zhang J et al, Probing cell-matrix interactions in RGD-decorated macroporous poly (ethylene glycol) hydrogels for 3D chondrocyte culture, *Biomed. Mater.* 10: 035016 (2015); and Costantini M et al., 3D bioprinting of BM-MSCs-loaded ECM biomimetic hydrogels for in vitro neocartilage formation, *Biofabrication* 8: 035002 (2016).

The extracellular matrix has been shown to provide important cues for cellular activities such as migration, proliferation and differentiation. Hynes R O, Extracellular matrix: not just pretty fibrils, *Science* 326: 1216-219 (2009). Collagen, proteoglycans and other non-collagenous proteins account for most of the dry weight of the chondral matrix (CM). Sophia Fox A J, et al. (2009); Aigner T and Stöve J, Collagens—major component of the physiological cartilage matrix, major target of cartilage degeneration, major tool in cartilage repair, *Adv. Drug Deliv. Rev.* 55: 1569-93 (2003); and Wilson R, et al., Proteomic analysis of cartilage proteins, *Methods* 45: 22-31 (2008).

Collagen II represents 90-95% of the collagen in the CM and forms fibrils and fibers intertwined with proteoglycan aggregates. Proteoglycans, such as aggrecan, are essential to retain water within the CM that is critical for maintaining the unique biomechanical properties of the articular cartilage. Chandran P L and Horkay F, Aggrecan, an unusual polyelectrolyte: review of solution behavior and physiological implications, *Acta Biomater.* 8: 3-12 (2012).

Also, various growth factors including transforming growth factor β (TGF-β), fibroblast growth factor (FGF), insulin-like growth factor (IGF), and Wnt protein are present in CM and are functionally implicated in the chondrogenesis of human mesenchymal stem cells (hMSCs). Fortier L A, et al., The Role of Growth Factors in Cartilage Repair, *Clin. Orthop. Relat. Res.* 469: 2706-15 (2011) and Danišovič L, et al., Growth factors and chondrogenic differentiation of mesenchymal stem cells *Tissue Cell.* 44: 69-73 (2012).

Microspheres can act as a vehicle for the controlled release of encapsulated growth factors due to their small dimensions and the corresponding high surface area, high loading capacity and their ability to protect the growth factors from degradation in vivo. Solorio L D, et al., High-density cell systems incorporating polymer microspheres as micro-environmental regulators in engineered cartilage tissues, *Tissue Eng. B* 19: 209-20 (2013); and Lam J, et al., Strategies for controlled delivery of biologics for cartilage repair, *Adv. Drug Deliv. Rev.* 84: 123-34 (2015).

As such, microspheres have been investigated for use in cartilage tissue engineering approaches. Id.; Eswaramoorthy R. et al., Sustained release of PTH (1-34) from PLGA microspheres suppresses osteoarthritis progression in rats, *Acta Biomater.* 8: 2254-62 (2012); El-Setouhy D A, et al., Leflunomide biodegradable microspheres intended for intra-articular administration: Development, anti-inflammatory activity and histopathological studies, *Int. J. Pharm.* 495: 664-70 (2015); Ko J Y, et al., Sulforaphane-PLGA microspheres for the intra-articular treatment of osteoarthritis, *Biomaterials* 34: 5359-68 (2013); and Liang C Z, et al., Dual release of dexamethasone and TGF-b3 from polymeric microspheres for stem cell matrix accumulation in a rat disc degeneration model, *Acta Biomater.* 9: 9423-33 (2013).

For example, one study showed that sustained release of PTH (1-34) from poly(lactide-co-glycolide) (PLGA) microspheres suppresses osteoarthritis progression in rats. Eswaramoorthy R, et al. (2012). In another study, the drug sulforaphane was encapsulated in PLGA microspheres for the intra-articular treatment of osteoarthritis. Ko J Y, et al. (2013).

Polymers such as poly(lactic acid) (PLA) and PLGA are FDA approved biodegradable polyesters that are used to produce microspheres and have been proposed as a support matrix for cartilage tissue engineering research. Chandran P L and Horkay F (2012); Eswaramoorthy R, et al. (2012); El-Setouhy D A, et al., (2015); and Ko J Y, et al. (2013).

Additionally, microspheres can be used as building blocks to form a hierarchically organized 3D scaffold by a bottom up approach. Lam J, et al. (2015); Spiller K L, et al., A novel method for the direct fabrication of growth factor-loaded microspheres within porous nondegradable hydrogels: controlled release for cartilage tissue engineering, *J. Control Release* 157: 39-45 (2012); and Hollister S J, Porous scaffold design for tissue engineering, *Nat. Mater.* 4: 518-24 (2005). One study demonstrated controlled release from porous non-degradable hydrogels containing growth factor-loaded microspheres that enhanced cartilage formation in athymic mice. Spiller K L et al. (2012). However, hydrogel scaffolds lack mechanical stability for skeletal tissue engineering.

A 3D printed scaffold, on the other hand, provides the possibility to select polymers for their desired mechanical function, mass transport properties (permeability and diffusion), and their ability to be manufactured into clinically relevant, complex 3D anatomical shapes for individualized applications. Hollister S J. (2005).

A need exists for improved 3D scaffolds for biomedical and therapeutic applications.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Disclosed herein is the controlled release of proteins, growth factors, cytokines, and proteoglycans from thermally stable matrix microspheres within polymer filaments, suitable for 3D printing and effectively enhancing migration, proliferation, and chondrogenesis of hMSCs in vitro.

In one embodiment, a decellularized matrix microsphere is provided, the decellularized matrix microsphere comprising a polymeric material and a donor tissue.

In another embodiment, a structure is provided, the structure comprising a plurality of decellularized matrix microspheres comprising a first polymer and a donor tissue; and a second polymer, wherein the decellularized matrix microspheres and the second polymer are in the form of a filament.

In another embodiment, a method of treating a subject suffering from a tissue injury is provided, the method comprising applying to the injury a structure comprising a plurality of decellularized matrix microspheres comprising a first polymer and a donor tissue; and a second polymer, wherein the decellularized matrix microspheres and the second polymer are in the form of a filament.

In another embodiment, a method of manufacturing a filament is provided, the method comprising: decellularizing a donor tissue; encapsulating the donor tissue in a first polymer to provide decellularized matrix microspheres; and co-extruding the decellularized matrix microspheres with a second polymer to provide the filament.

shows collagen deposition by cells using biochemical assays. Values represent mean±SD. (e) illustrates reverse transcriptase-polymerase chain reaction (RT-PCR) quantification of cartilage matrix genes, hypertrophy related and osteogenic genes of the cells grown in presence of microspheres in basal or chondrogenic induction media at day 21. Data is shown as mean±SD. BM, basal media; CIM, chondrogenic induction media; MS(−), blank microspheres; MS+dCM, microspheres containing decellularized chondral matrix. (*$p<0.05$, $p<0.01$, *$p<0.001$, ****$p<0.0001$).

Figure 6:
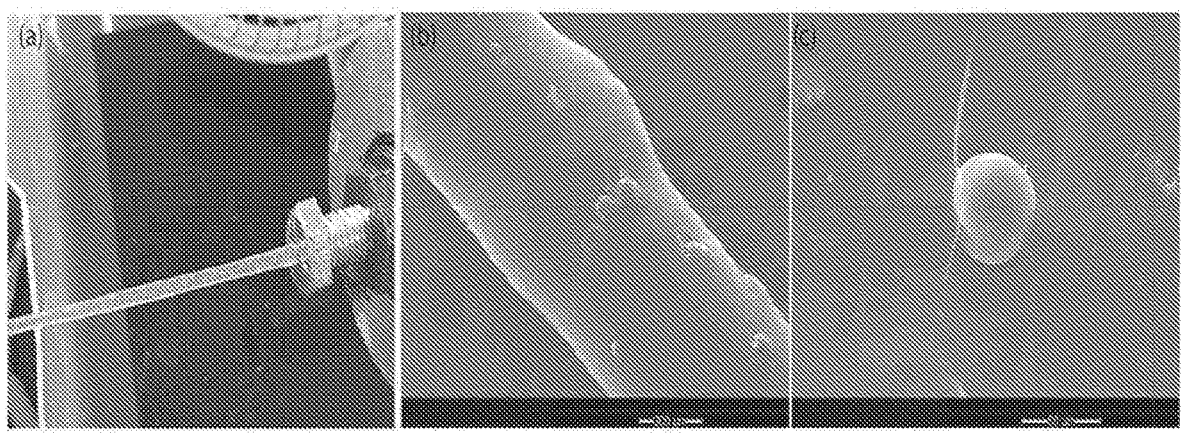

FIG. 6. (a) illustrates PCL Filament production via melt extrusion; (b) provides representative SEM micrograph of PCL filament with microspheres, scale bar 200µ; and (c) shows a higher magnification of (b), scale bar 50µ.

Figure 7:
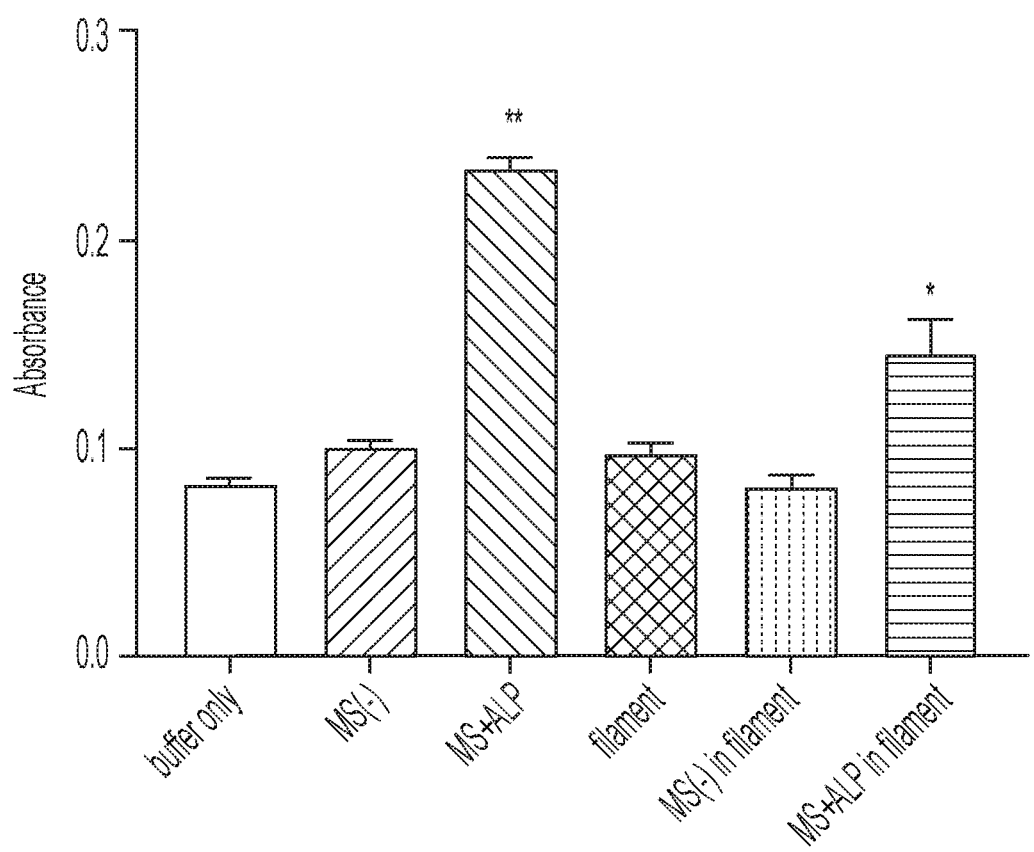

FIG. 7 illustrates results from an alkaline phosphatase (ALP) assay performed to test the functionality of microspheres and filaments after fabrication. MS(−), blank microspheres; MS+ALP, microspheres encapsulating ALP; MS(−) in filament, filament containing blank microspheres; MS+ALP in filament, filament containing ALP within microspheres. Values are mean±SD, n=3. *$p<0.05$ indicates significant difference of all groups w.r.t MS+ALP in filament; **$p<0.01$ indicates significant difference between MS+ALP group and MS+ALP in filament group.

Figure 8:
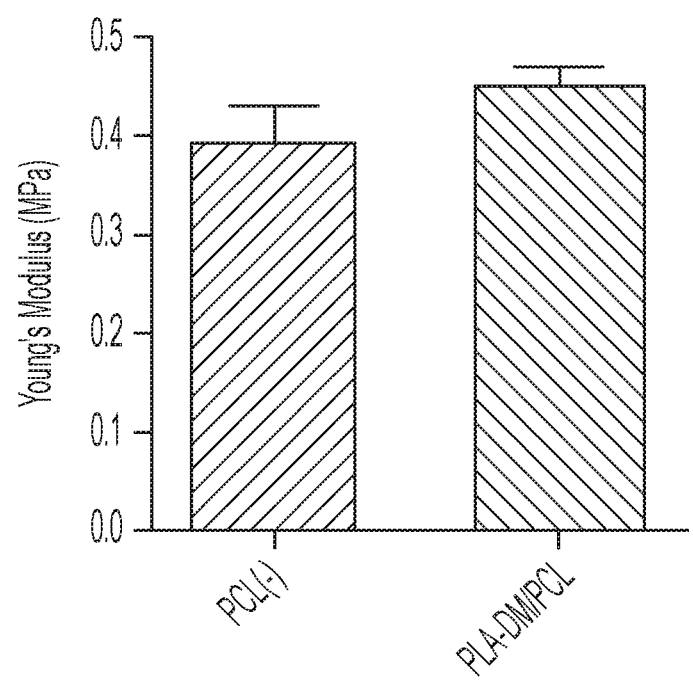

FIG. 8 provides the results of the mechanical testing and demonstrates that the addition of microspheres to the PCL scaffolds had no significant impact on the modulus of elasticity of the scaffolds.

Figure 9:
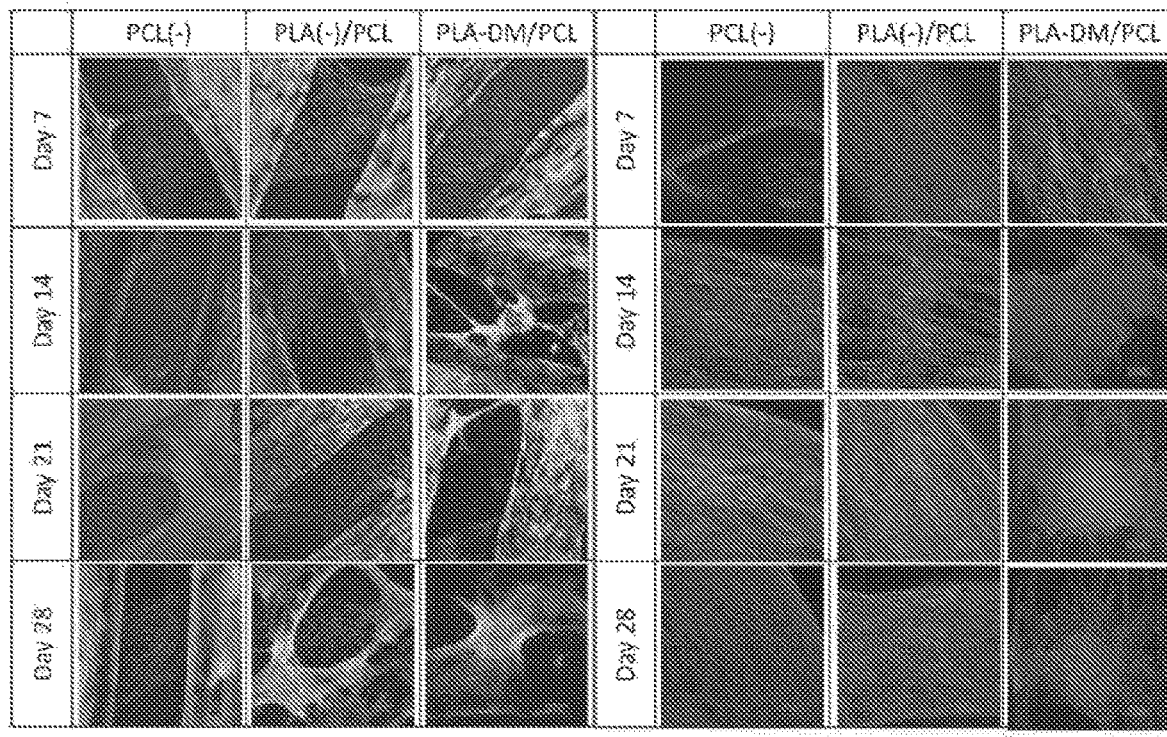
Figure 9:
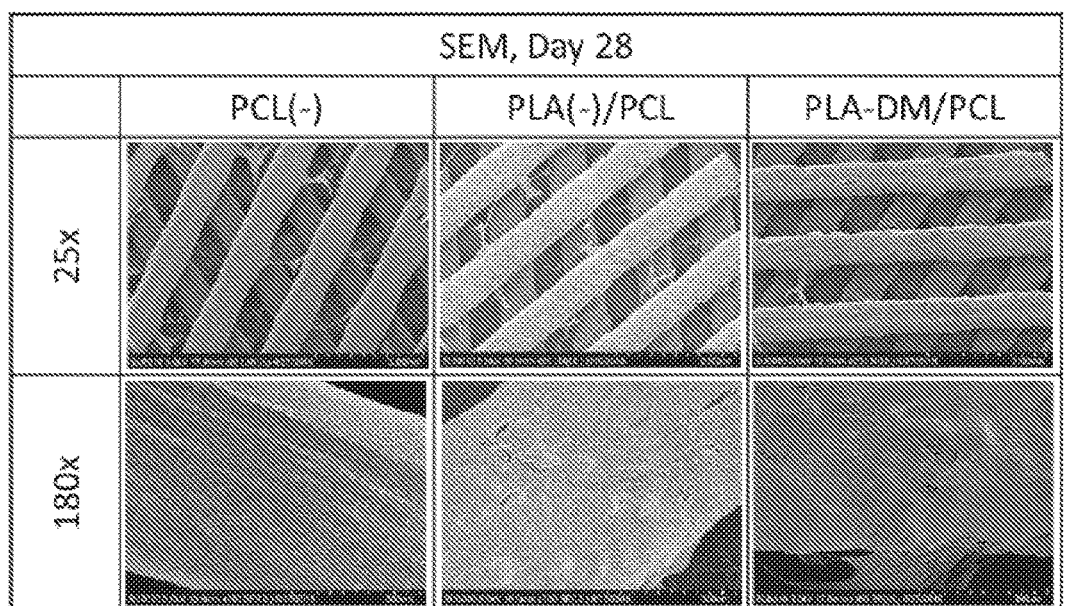

FIG. 9 provides the results of the imaging tests, according to one embodiment. (a) illustrates results from the live/dead assay and shows that living cells were present on the surface of the scaffold throughout the culture period. (b) provides focal adhesion imaging and shows that cells on PLA-DM/PCL formed aggregates while the other groups formed more homogenous, fibrous structures. (c) SEM pictures show the deposition of extracellular matrix on scaffolds after 28 days and attachment of cells to the scaffold surface where microspheres are present in PLA(−)/PCL and PLA-DM/PCL and absent in the PCL(−) as expected.

Figure 10:
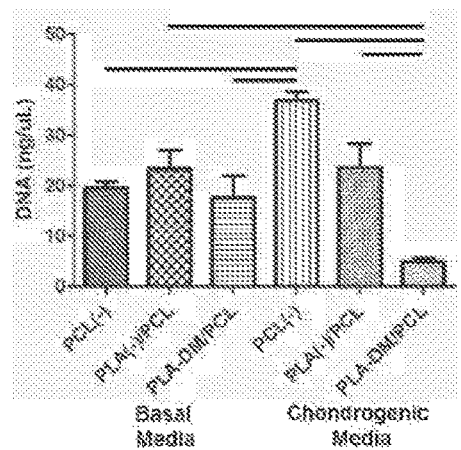
Figure 10:
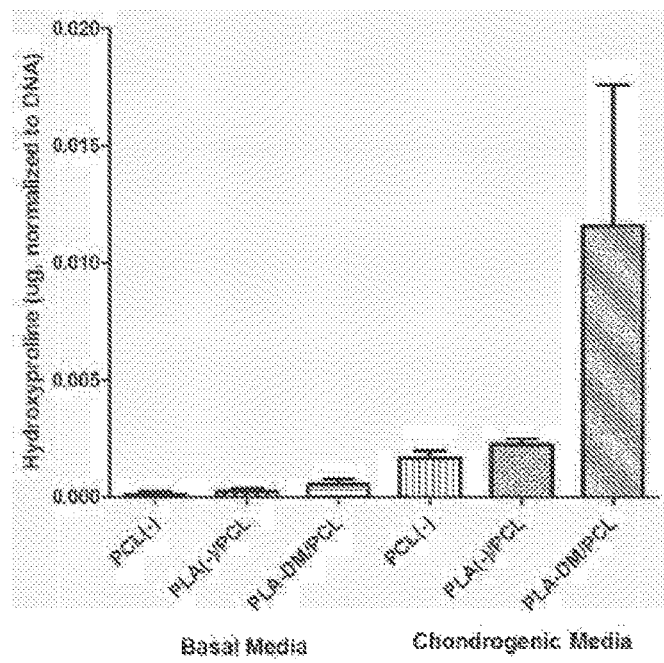

FIG. 10 provides the results from biochemical assays. These results demonstrate that there were significant differences in DNA content between the scaffold groups (a) and no significant difference in hydroxyproline accumulation (b).

Figure 11:
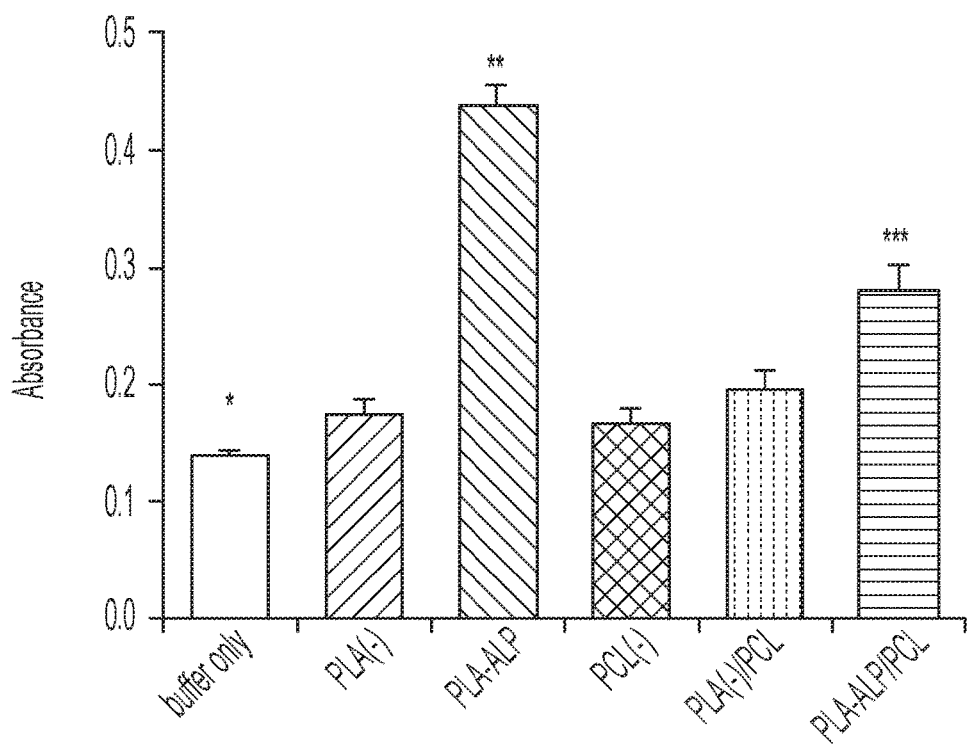

FIG. 11 shows that ALP remained functional after the printing process, as evidenced by its catalysis of the colorimeteric reaction from p-nitrophenyl phosphate to p-nitrophenol and inorganic phosphate.

Figure 12:
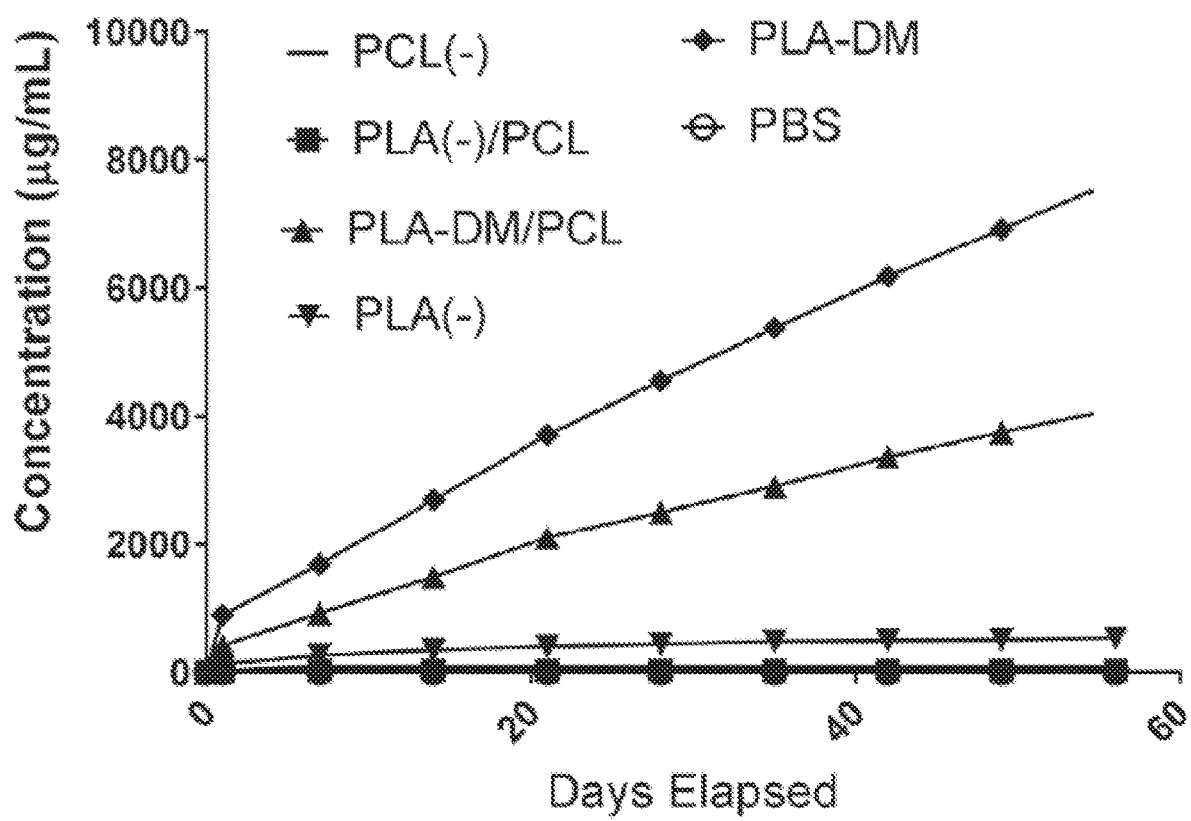

FIG. 12 illustrates that decellularized cartilage matrix (DM) contained in microspheres and DM contained in printed scaffolds both showed sustained release of matrix proteins (via Lowry Assay) over the 8 week period.

Figure 13:
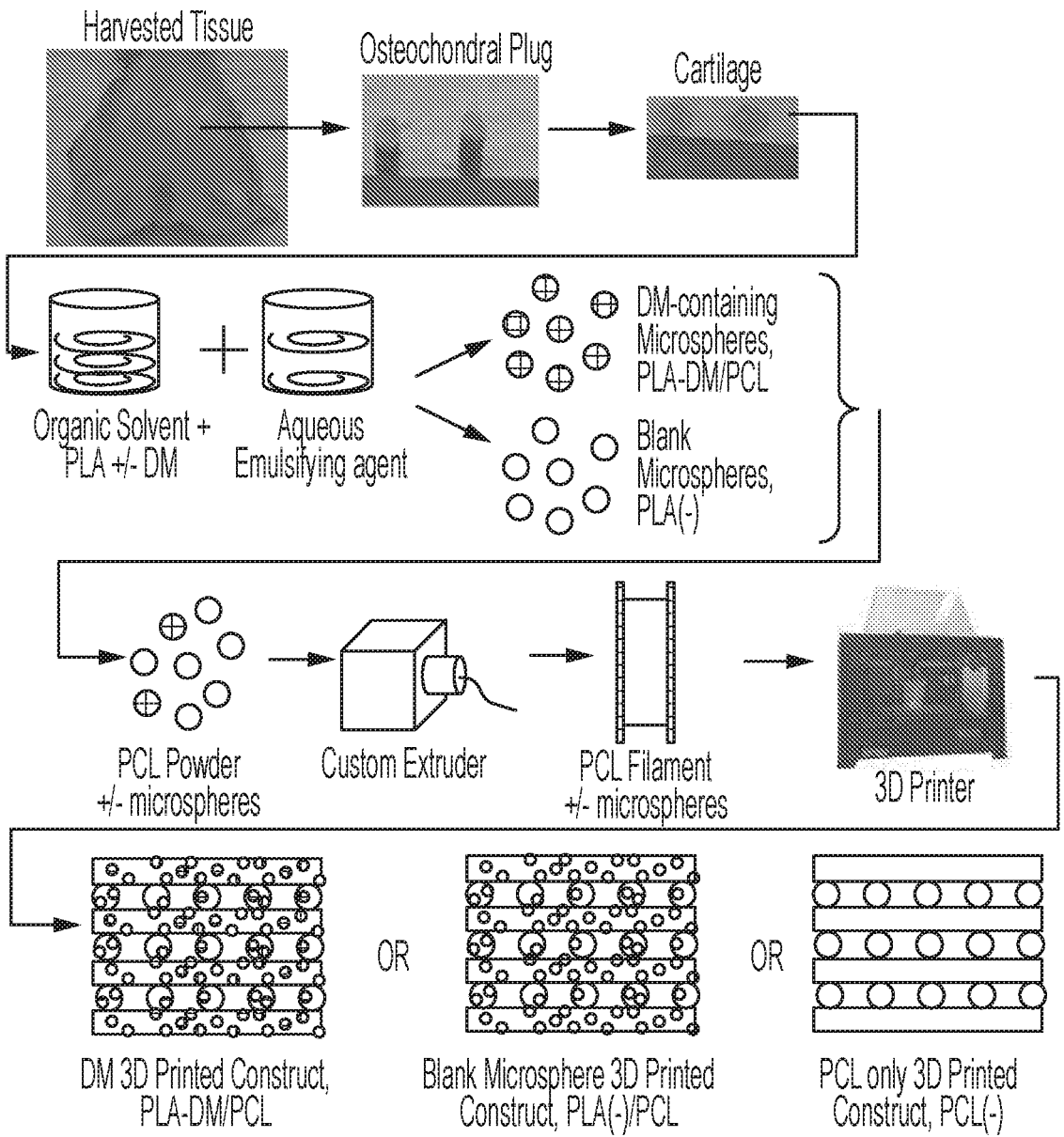

FIG. 13 is a schematic representation of the process according to one embodiment. In this embodiment, porcine cartilage is harvested and decellularized in a series of rinses and washes. The solubilized tissue is then encapsulated in PLA, extruded with PCT, and printed into the desired geometry.

SEQUENCE LISTING

Applicant hereby incorporates by reference a CRF sequence listing submitted herewith having a file name 10738-674_Sequence_Listing.txt created on Oct. 26, 2018.

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NO: 1 represents a forward primer for ACAN.
SEQ ID NO: 2 represents a reverse primer for ACAN.
SEQ ID NO: 3 represents a forward primer for SOX9.
SEQ ID NO: 4 represents a reverse primer for SOX9.
SEQ ID NO: 5 represents a forward primer for COL II.
SEQ ID NO: 6 represents a reverse primer for COL II.
SEQ ID NO: 7 represents a forward primer for COL I.
SEQ ID NO: 8 represents a reverse primer for COL I.
SEQ ID NO: 9 represents a forward primer for COL X.
SEQ ID NO: 10 represents a reverse primer for COL X.
SEQ ID NO: 11 represents a forward primer for OCN.
SEQ ID NO: 12 represents a reverse primer for OCN.
SEQ ID NO: 13 represents a forward primer for RUNX2.
SEQ ID NO: 14 represents a reverse primer for RUNX2.
SEQ ID NO: 15 represents a forward primer for ACTIN.
SEQ ID NO: 16 represents a reverse primer for ACTIN.

DETAILED DESCRIPTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The inventors have successfully decellularized the chondral matrix (dCM) and characterized it biochemically and histologically. Thereafter, the dCM was encapsulated in PLA microspheres (MS+dCM). The sustained release of encapsulated growth factors from MS+dCM resulted in enhanced cell migration and higher expression of cartilage specific markers when cultured with hMSCs in comparison to hMSCs cultured in their absence. Subsequently, microspheres containing alkaline phosphatase (MS+ALP), a surrogate for dCM proteins, were incorporated within poly (caprolactone) filaments and the enzyme remained functional after filament production by melt extrusion. The establishment of a novel, thermally stable process for producing filaments containing chondroinductive microspheres supports a clinically-relevant, 3D scaffold fabricated from them for osteochondral regeneration and repair.

Development of a novel, biomimetic three-dimensional construct of clinically-relevant size and mechanical properties that can induce chondral differentiation after implantation has the potential to significantly advance the treatment of patients suffering from large osteochondral injuries. The critical need for such a construct provided motivation to engineer a filament for subsequent scaffold production that is capable of promoting chondral progenitor cell viability, homing and cartilage specific differentiation.

3D scaffolds containing bioactive microspheres are a promising alternative to current cartilage repair techniques due to their inherent ability to control the release of a wide array of bioactive factors. The use of decellularized cartilage matrix (dCM) instead of native cartilage for encapsulation in microspheres is advantageous from clinical and commercial standpoints due to decreased immunogenicity and pathogenicity, as well as the ability to store the material for long periods of time at a surgical center.

The inventors of the instant application utilized decellularization to remove cellular components from articular cartilage while preserving structural proteins and other molecules of interest such as sGAGs, growth factors, and cytokines. Subsequently, decellularized cartilage matrix was encapsulated within PLA microspheres. Sustained delivery of proteins from the microspheres increased the homing, viability, and chondrogenic differentiation of hMSCs in vitro compared to controls.

Using this information, the inventors of the instant application fabricated a hybrid PCL filament containing microsphere encapsulated ALP enzyme as a surrogate for assessing the thermal stability of MS+dCM after production by melt extrusion. The observed maintenance of ALP enzyme activity in the filaments provides evidence that the extrusion process of filament production does not impair biological activity of the encapsulated proteins.

In various embodiments, provided herein are filament containing inductive microspheres capable of being fabricated into 3D printed scaffolds for use both in vitro and in vivo as a treatment for large osteochondral injuries.

Figure 1:
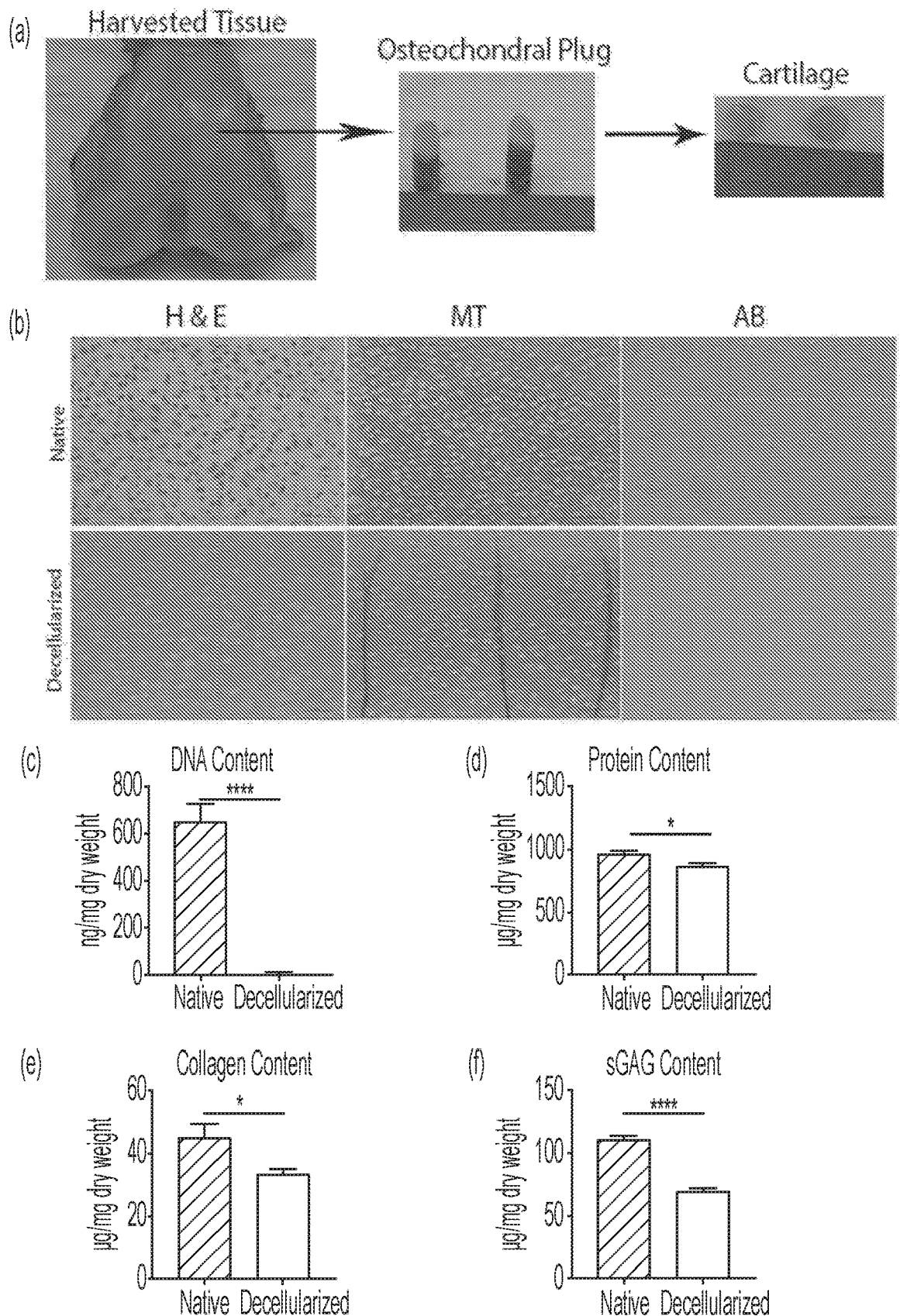
FIG. 1. (a) provides a schematic representation of isolation of articular cartilage from porcine hind limbs, according to one embodiment. (b) provides histology of native and decellularized cartilage assessed by H&E, MT and AB. The biochemical composition of the native and decellularized cartilage matrix was evaluated by (c) DNA content (d) Total protein content (e) Collagen content (f) Sulfated GAGs content. Data is shown as mean±SD. (*$p<0.05$, ****$p<0.0001$). H&E, Hematoxylin and Eosin; MT, Masson Trichrome; AB, Alcian Blue staining.

The inventors have accomplished the near complete removal of nuclear material qualitatively by histological staining and quantitatively by biochemical methods, while preserving important chondral matrix proteins and sGAGs (FIG. 1). The collagen molecules in the cartilage matrix contribute to the structural organization of the tissue while sGAGs interact with other proteins and provide compressive strength to the matrix. In addition to collagen and sGAGs, growth factors and cytokines control many cartilage progenitor cell functions (e.g., homing, attachment, growth and differentiation).

Figure 2:
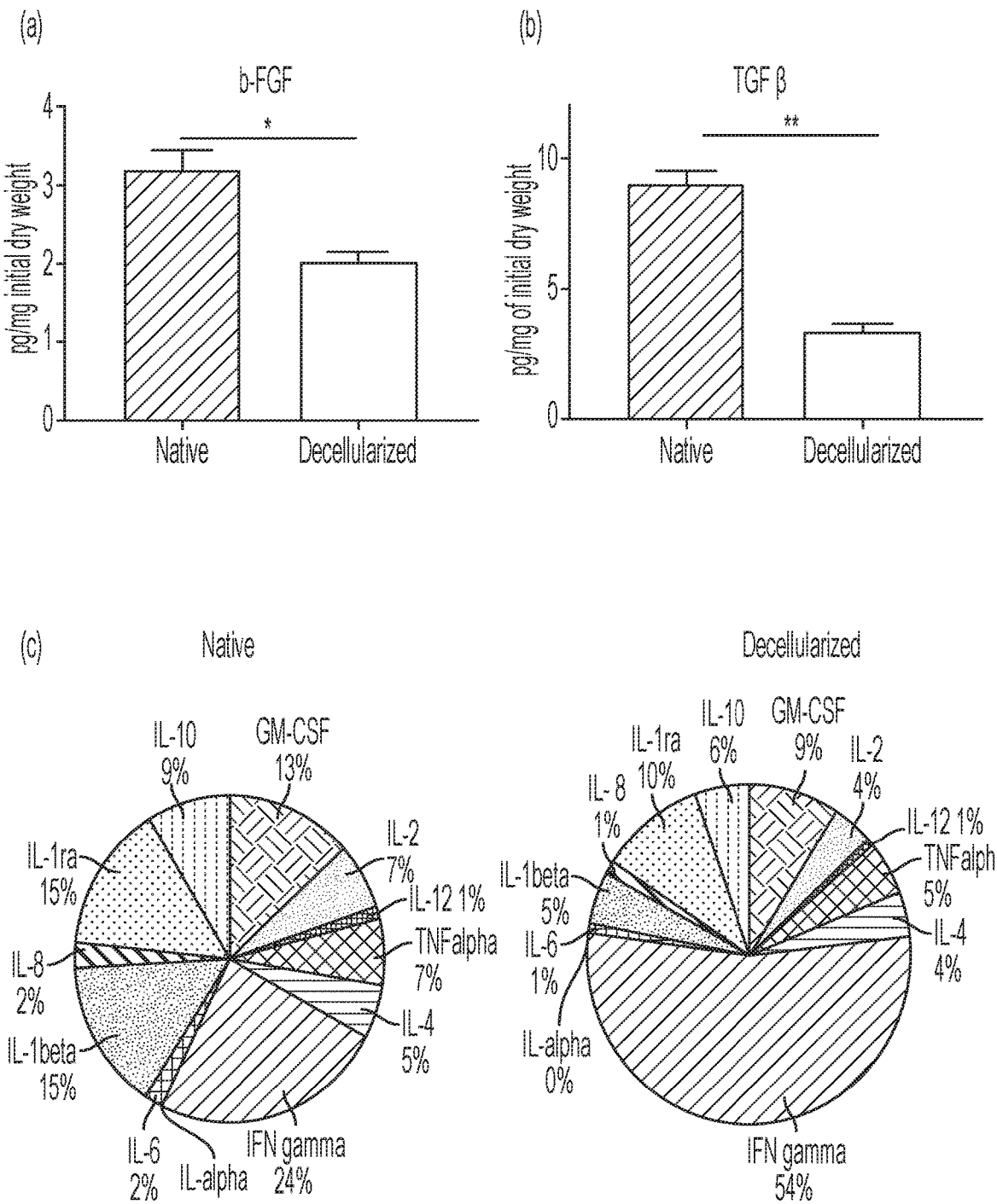
FIG. 2 illustrates the growth factor concentrations in urea-heparin extracts of native and decellularized cartilage matrix isolated from porcine hind limbs, according to one embodiment. (a) shows b-FGF; (b) shows TGF β and (c) shows Chemokines. Data is provided as mean±SD. (*$p<0.05$, **$p<0.01$).

The retention of multiple, previously identified growth factors and cytokines thought to be important in these roles after the decellularization process (FIG. 2). The rationale for selection of the estimation of specific growth factors (TGF-$\beta$ and bFGF) was based on their established contribution to cell recruitment, proliferation, and condensation of hMSCs, in addition to chondroblast differentiation to chondrocytes. While not desiring to be bound by theory, it is believed that other associated growth factors, potentially important to cartilage formation, are also present and retained after decellularization.

The bioactive dCM containing multiple growth factors and cytokines was encapsulated efficiently in PLA microspheres. Release of the encapsulated growth factors occurred with an initial burst followed by a sustained release throughout the observation period. The extent of the initial burst release depends on the encapsulated protein charge, polymer composition, hydrophilicity, and other factors. The subsequent release of proteins from the MS+dCM is influenced mainly by two principal mechanisms: (1) diffusion of the dCM proteins from the porous surface of the microspheres and (2) release of the dCM protein upon the erosion of the PLA polymer matrix. Overall, the conditions for protein release were observed to be favorable for the system developed herein and had an observable and measurable effect upon cells exposed to them, indicating that they are bioactive.

To determine whether MS+dCM were capable of supporting cell attachment, survival, and growth, hMSCs were cultured for 7 days on the microspheres. Both MS+dCM and MS(−) were cytocompatible in vitro and provided sites for cell attachment as evidenced from focal adhesion staining and SEM studies. Sustained delivery of the proteins and growth factors from MS+dCM promoted higher cell migration compared to MS(−).

This is in agreement with a previous study by Ponte et al. that demonstrated the ability of bone marrow hMSCs to migrate in response to a large set of chemotactic factors, including both growth factor and chemokines in vitro. It was also observed that the sustained delivery of proteins from MS+dCM promoted the differentiation of hMSCs, as evidenced by upregulation of the cartilage specific marker expression in comparison to controls.

Notably, a significantly higher level of cartilage matrix deposition by hMSCs was observed by histology and biochemical quantification when hMSCs were cultured in presence of MS+dCM compared to controls. It has been previously demonstrated that decellularized tissue extracellular matrix is beneficial for cellular maturation and precursor/stem cell differentiation. See, Bhattacharjee M, et al. (2016).

The most striking finding of this study was observed in hMSC pellets cultured in presence of MS+dCM in basal media which showed reduced expression of COL X, a hypertrophy related gene associated with chondrocyte dedifferentiation, when compared to hMSC pellets cultured in the presence of MS+dCM in traditional chondrogenic induction media. This result highlights the ability of the dCM to induce a more desirable chondrocyte phenotype for cartilage repair without the need for additional exposure to a traditional chondroinductive media or chondroinductive supplements.

Moreover, the chondroinductive media appears to be deleterious to the desired chondral differentiation pathway; instead it appears to induce cells to undergo hypertrophy associated with endochondral ossification. Therefore, not only does the use of the MS+dCM forego the need for traditional chondroinductive media that induces unfavorable ossification, it also supports cell differentiation toward the desired cartilage phenotype. These intrinsic properties are both necessary and very advantageous with regard to clinical translation and commercialization.

Subsequently, microspheres encapsulating the enzyme ALP were incorporated within PCL filaments, as an easily tested functional surrogate of the dCM proteins, to assess the thermal stability and maintenance of bioactivity of the dCM the during melt extrusion process of filament fabrication. Based on the enzyme quantification assay, encapsulated ALP in the filaments was stable and could hydrolyze its substrate effectively forming a yellow colored product, the absorbance of which was significantly higher than that of appropriate controls, indicating that even a large, complex protein such as an enzyme is preserved with respect to functionality and therefore, catalytic structure (FIG. 7).

The bioactive PCL filaments incorporated with MS+dCM combine the advantages of chondroinduction, sustained, extended release, and protection from degradation during filament fabrication, which is worthy of further development and translational applications in osteochondral tissue engineering. Polymers such as PCL are known to have sufficient thermoplasticity to make them suitable for 3D printing. The 3D printed PCL scaffolds have also been widely utilized in various load-bearing, skeletal tissue engineering applications. Current tissue engineering approaches to osteochondral injuries lack clinically relevant size and are unable to withstand intra-articular forces encountered in large joints. Therefore, our future studies will investigate the fabrication of 3D scaffolds of clinically relevant size and mechanical properties formed using the hybrid PCL filament containing MS+dCM.

As disclosed herein, articular cartilage was decellularized preserving a majority of the inherent proteins, cytokines, growth factors and sGAGs. The decellularized cartilage matrix (dCM) was then encapsulated in poly(lactic acid) microspheres (MS+dCM) via double emulsion. Blank microspheres without dCM, MS(−), were also produced. The microspheres were spherical in shape and protein encapsulation efficiency within MS+dCM was about 63.4%. The sustained release of proteins from MS+dCM was observed over 4 weeks in vitro. Both MS+dCM and MS(−) were cytocompatible. The sustained delivery of retained growth factors and cytokines from MS+dCM promoted cell migration in contrast to MS(−). Subsequently, chondrogenesis of hMSCs was upregulated in presence of MS+dCM as evidenced from immunohistochemistry, biochemical quantification and qPCR studies.

Collagen II, aggrecan and SOX 9 gene expression were increased in the presence of MS+dCM by an order or more in magnitude compared to MS(−) with concomitant downregulation of hypertrophic genes (COL X) despite being cultured in the absence of chondrogenic media, (p<0.05).

Microspheres containing alkaline phosphatase (MS+ALP), a surrogate to assess the thermal stability of dCM proteins, incorporated within polycaprolactone filaments showed that the enzyme remained functional after filament production by melt extrusion. The establishment of a novel, thermally stable process for producing filaments containing chondroinductive microspheres provides evidence supporting subsequent development of a clinically-relevant, 3D scaffold fabricated from them for osteochondral regeneration and repair.

In embodiments, a decellularized matrix microsphere is provided comprising a polymeric material and a biological material. In embodiments, the biological material comprises one or more of tissues, cells, growth factors, proteins, collagen, pharmaceutical agents, and biological agents. See, for example, Howard D, et al, Tissue engineering: strategies, stem cells, and scaffolds, *J. Anatomy* 213(1): 66-72 (2008).

In embodiments, a decellularized matrix microsphere is provided comprising a polymeric material and a donor tissue.

In embodiments, a donor tissue comprises chondral tissue, tracheal tissue, bone tissue, cardiovascular tissue, nerve tissue, muscle tissue, skin, organ tissue, or a tissue derived from mesodermal, ectodermal, or mesenchymal origin. In embodiments, the decellularized tissue may be obtained from allogenic, xenogenic, or autograft sources.

In embodiments, the microspheres and structures disclosed herein can be combined with cells from allogenic, xenogenic, or autograft sources, including but not limited to, stem cells, induced pluripotent stem cells (IPSCs), and the like.

In embodiments, the polymeric material comprises one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, polyamide, and copolymers thereof or stereoisomers thereof. In a specific embodiment, the polymeric material is polylactic acid (PLA).

In embodiments, a structure is provided, the structure comprising a plurality of decellularized matrix microspheres comprising a first polymer and a biological material as previously described; and a second polymer, wherein the decellularized matrix microspheres and the second polymer are in the form of a filament.

In embodiments, a structure is provided, the structure comprising a plurality of decellularized matrix microspheres comprising a first polymer and a donor tissue; and a second polymer, wherein the decellularized matrix microspheres and the second polymer are in the form of a filament.

In embodiments, donor tissue comprises chondral tissue, tracheal tissue, bone tissue, cardiovascular tissue, nerve tissue, muscle tissue, skin, organ tissue, or a tissue derived from mesodermal, ectodermal, or mesenchymal origin. In embodiments, the decellularized tissue may be obtained from allogenic, xenogenic, or autograft sources.

In embodiments, the microspheres and structures disclosed herein can be combined with cells from allogenic, xenogenic, or autograft sources, including but not limited to, stem cells, induced pluripotent stem cells (IPSCs), and the like.

In embodiments, the plurality of decellularized matrix microspheres and the second polymer are at a weight ratio of about 1:4.

In embodiments, the first polymer and the second polymer are independently selected from one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, nylons, and copolymers thereof or stereoisomers thereof. In a specific embodiment, the first polymer is PLA. In another specific embodiment, the second polymer is PCL. The first polymer and the second polymer optionally comprise the same polymer(s), or optionally comprise different polymer(s).

In embodiments, a 3D scaffold is provided, comprising a structure comprising a plurality of decellularized matrix microspheres comprising a first polymer and a biological material as previously described; and a second polymer, wherein the decellularized matrix microspheres and the second polymer are in the form of a filament.

In embodiments, a 3D scaffold mimicking native tissue is provided, comprising decellularized matrix microspheres, wherein the decellularized matrix microspheres comprise donor tissue encapsulated in a polymer.

In embodiments, a 3D scaffold is provided, comprising a structure comprising a plurality of decellularized matrix microspheres comprising a first polymer and a donor tissue; and a second polymer, wherein the decellularized matrix microspheres and the second polymer are in the form of a filament.

In another embodiment, a method of treating a subject suffering from a tissue injury is provided, the method comprising applying to the injury a structure comprising a plurality of decellularized matrix microspheres comprising a first polymer and a biological material; and a second polymer, wherein the decellularized matrix microspheres and the second polymer are in the form of a filament.

In another embodiment, a method of treating a subject suffering from a tissue injury is provided, the method comprising applying to the injury a structure comprising a plurality of decellularized matrix microspheres comprising a first polymer and a donor tissue; and a second polymer, wherein the decellularized matrix microspheres and the second polymer are in the form of a filament. In a specific embodiment, the tissue injury is a chondral injury and the donor tissue comprises chondral tissue. In a very specific embodiment, the chondral tissue comprises porcine osteochondral tissue; however, the skilled artisan will appreciate that donor tissue may be obtained from a variety of donors. In embodiments, the treatment methods induce chondrogenesis in the subject treated.

In another embodiment, a method of manufacturing a filament is provided, the method comprising: decellularizing a biological material; encapsulating the biological material in a first polymer to provide decellularized matrix microspheres; and co-extruding the decellularized matrix microspheres with a second polymer to provide the filament.

In another embodiment, a method of manufacturing a filament is provided, the method comprising: decellularizing a donor tissue; encapsulating the donor tissue in a first polymer to provide decellularized matrix microspheres; and co-extruding the decellularized matrix microspheres with a second polymer to provide the filament.

In embodiments, the donor tissue comprises chondral tissue, tracheal tissue, bone tissue, cardiovascular tissue, nerve tissue, muscle tissue, skin, organ tissue, one or more growth factors, one or more cytokines, or a tissue derived from mesodermal, ectodermal, or mesenchymal origin. In a specific embodiment, the donor tissue is chondral tissue.

In embodiments, the first polymer and the second polymer are independently selected from one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, nylons, and copolymers thereof or stereoisomers thereof. In a specific embodiment, the first polymer is PLA. In another specific embodiment, the second polymer is PCL. The first polymer and the second polymer optionally comprise the same polymer(s), or optionally comprise different polymer(s).

In embodiments, a 3D scaffold comprising the filament made by any of the disclosed methods is provided.

In another embodiment, a 3D scaffold mimicking native chondral tissue is provided, comprising decellularized matrix microspheres, wherein the decellularized matrix microspheres comprise decellularized donor cartilage encapsulated in polylactic acid (PLA).

In embodiments, the decellularized matrix microspheres are co-extruded with polycaprolactone (PCL) powder at a weight ratio of about 1:4 to create a PLA-DM/PCL filament for a 3D printer.

In another embodiment, a method for treating an osteochondral injury (OCI) in a subject in need thereof is provided, comprising applying a biphasic 3D scaffold incorporating decellularized osteochondral matrix (dOCM) microspheres to the injury. In embodiments, the biphasic 3D scaffold comprises PLA microspheres containing dOCM. In embodiments, the dOCM in the PLA microspheres is from porcine osteochondral (OC) tissue. However, the skilled artisan will appreciate that various osteochondral tissue sources are suitable for use in the scaffolds and methods disclosed herein. In embodiments, the biphasic 3D scaffold is chondroinductive. In embodiments, the osteochondral injury is greater than 2.5 $cm^2$.

In another embodiment, a method for manufacturing a 3D scaffold mimicking native tissue is provided, comprising: decellularizing a donor structural tissue; encapsulating the decellularized donor structural tissue in polylactic acid (PLA) microspheres to provide decellularized matrix microspheres; co-extruding the decellularized matrix microspheres with polycaprolactone (PCL) powder to create a filament; and forming a scaffold comprising the filament via 3D printing. The 3D scaffolds disclosed herein enhance migration, proliferation, and chondrogenesis of human mesenchymal stem cells (hMSCs).

In embodiments, the decellularized donor structural tissue comprises tracheal tissue, chondral matrix proteins, sulphated glycosaminoglycans (sGAGs), cartilage, growth factors, cytokines, proteoglycans, and combinations thereof.

In embodiments, the weight ratio of decellularized matrix microspheres to polycaprolactone powder in the co-extruding step is about 1:4.

In another embodiment, a method for manufacturing a 3D scaffold mimicking native chondral tissue is provided, comprising: decellularizing donor cartilage; encapsulating the decellularized donor cartilage in polylactic acid (PLA) microspheres to provide decellularized matrix microspheres; co-extruding the decellularized matrix microspheres with polycaprolactone (PCL) powder to create a filament; and forming a scaffold comprising the filament via 3D printing. The 3D scaffolds disclosed herein enhance migration, proliferation and chondrogenesis of human mesenchymal stem cells (hMSCs).

Various aspects of the present disclosure are illustrated by the following non-limiting examples. The examples are for illustrative purposes and are not a limitation on any practice of the present disclosure. It will be understood that variations and modifications can be made without departing from the spirit and scope of the disclosure. All reagents are commercially available unless otherwise indicated, and a person of ordinary skill in the art readily understands where such reagents may be obtained.

EXPERIMENTAL

Example 1: Cartilage Harvest and Decellularization

The hind limbs of pigs were provided by the Center for Surgical Innovation, University of Cincinnati. The limbs were cleaned to remove excess blood and disinfected using aseptic techniques. The osteochondral plugs of 8 mm diameter were harvested from the femoral condyle using an Osteochondral Autograft Transfer (OAT) system.

The cartilage was then excised from the bone and were placed in sterile 15 mL conical tubes (Falcon) and stored at −80° C. until further use. The cartilage tissue was decellularized similar to the process previously described. See, Whitlock P W, et al., A naturally derived, cytocompatible, and architecturally optimized scaffold for tendon and ligament regeneration, *Biomaterials* 28: 4321-29 (2007).

Cartilage tissues were exposed to a series of solutions with continuous stirring in a rotating shaker (New Brunswick Scientific) at 200 rpm, 37° C. First, the tissues were immersed in 100 mL of nuclease free distilled water (diH$_2$O; Promega) for 24 h following which water was discarded and the cycle was repeated. Thereafter, 100 mL of 0.05% trypsin, 0.5 mm tetrasodium EDTA (Sigma, St. Louis, Mo.), and 4 mM sodium bicarbonate (Sigma) prepared in Hank's balanced salt solution (Gibco) was added to the tissues. The tissues were then placed onto a rotating shaker for 4 h.

The trypsin activity was halted by incubating the tissues in 100 mL of Dulbecco's modified Eagle's medium (DMEM) high-glucose (Gibco) containing 10% fetal bovine serum (FBS, Valley Labs, Winchester, Va.) and 100 IU/mL penicillin, 100 µg/mL streptomycin, 0.25 µg/mL amphotericin B (Gibco) for 24 h.

After 24 h, the DMEM-FBS solution was discarded and replaced with 100 mL of deionized H$_2$O (diH$_2$O) and placed back onto the rotary shaker for 24 h. The water wash was discarded and 100 mL of 1.5% peracetic acid (Sigma) solution with 2.0% Triton X-100 (Sigma) in diH$_2$O was added and the tissues were placed onto the rotary shaker for 4 h.

The solution was discarded and two 100 mL diH$_2$O washes were accomplished, each for 12 h at 37° C. on the rotary shaker. At the end of the second wash, the tissues were removed and placed in a 15 mL conical tube and frozen at −80° C. for 24 h.

Example 2: Histologic Analysis of Native and Decellularized Tissues

Fresh-frozen native and decellularized chondral tissues were placed in 10% phosphate-buffered formalin (Sigma) at room temperature for 24 h and were then processed for histology.

The tissues were dehydrated in a graded series of ethanol, soaked in xylene, embedded in paraffin and sliced with a microtome to obtain 5.0 µm thick, longitudinal sections. These sections were then mounted on slides and stained using hematoxylin and eosin (H&E), Masson's trichrome (MT) and alcian blue. The stained sections were then assessed under a light microscope (Nikon 90i).

Example 3: Biochemical Evaluation of Native and Decellularized Tissues

The fresh-frozen native and decellularized cartilage tissues (n=10) were lyophilized (Labconco, Freeze Dry System, Kansas City, Mo.) for 72 h to achieve equivalent weight for DNA content evaluation. Total DNA was isolated from the cartilage tissues (Approximately 25 mg each) using a commercially available kit (DNeasy, Qiagen, Valencia, Calif.).

The total DNA content was measured by absorption at 260 nm using a spectrophotometer (Thermo Spectronic, Biomate 3, Rochester, N.Y.) and normalized to initial dry weight of the samples.

The lyophilized native and decellularized tissues were digested using pepsin (Sigma-Aldrich, St. Louis, Mo.)-HCl. In brief, 20 mg of the lyophilized samples was digested with 1 mg of pepsin in 0.01 N HCl (Sigma-Aldrich) for 48 h at room temperature under constant stirring. The partially digested samples were diluted with 10×PBS and 0.1 N NaOH.

Total protein content in the tissues was estimated using total protein assay kit, Onishi & Barr Modification (Sigma) following the manufacturer protocol. In this method, biuret reagent reacts with peptide bonds to yield a purple-blue complex, the color of which is intensified by the addition of phenol reagent. Biuret reagent was added to native and decellularized digested samples (n=8), mixed well and allowed to stand for 10 min. Thereafter, 100 µL of folin & ciocataceu reagent was added and allowed to incubate at room temperature for 30 min.

Absorbance was taken at 700 nm using a spectrophotometer (Thermo Spectronic, Biomate 3, Rochester, N.Y.) with blank as 0.85% sodium chloride. The protein concentration (µg/mL) of the native and decellularized tissue was obtained from the calibration curve of standard protein sample and normalized to initial dry weight of the samples.

The pepsin digested samples were further used for collagen estimation using Hydroxyproline Assay kit (Sigma). The digested samples were acid-hydrolyzed and reacted with a chloramine-T and p-dimethylaminobenzaldehyde solution to determine the quantity of hydroxyproline. The absorbance was detected with a microplate reader (Bio-Rad) at 560 nm and concentration was calculated from a series of concentrations of hydroxyproline. The hydroxyproline content was converted to that of total collagen using a mass ratio of 1:10.

Sulphated Glycosaminoglycans (sGAGs) matrix components were quantified via spectrophotometry using the Blyscan assay kit (Biocolor Ltd, Carrickfergus, United Kingdom), according to the manufacturer's instructions. Approximately 25 mg of lyophilized native and decellularized chondral tissues (n=4) were digested in papain (Sigma, St. Louis, Mo.) extraction buffer prepared in 50 mM phosphate buffer (pH 6.5), containing 5 mM cysteine HCl and 5 mM EDTA solution at 65° C. for 16 h. 100 µL of the lysate solution was then mixed with 1 mL blyscan dye reagent to allow blyscan dye to bind to the sGAG of chondral tissues and precipitate out of solution.

Alter centrifugation, the sGAG-dye complex was obtained. The unbound dye solution was removed and lint of dissociation reagent was added to release the dye, 200 μL of the resulting solution was transferred into a 96-well plate and absorbance was measured at 656 nm using plate reader and the concentration was represented as μg of sGAG/mg dry weight.

Example 4: Growth Factor and Chemokine Quantification of Native and Decellularized Tissues The urea-heparin extraction protocol was performed as described earlier. The fresh-frozen native and decellularized cartilage tissues were lyophilized, mixed with dry ice and powdered using a cryogenic tissue grinder (Biospec Products Bartlesville, Okla.) for 15 min. The resulting samples were then stored in a Ziploc bag at 4° C. overnight to evaporate the dry ice to obtain native (nCM) and decellularized (dCM) cartilage matrix powder.

400 mg of powdered nCM and dCM was then added in 6 mL of urea-heparin extraction buffer consisting of 2M urea (Sigma-Aldrich) and 5 mg/mL heparin (Sigma-Aldrich) in 50 mM Tris (Sigma-Aldrich) with a protease inhibitor from Sigma-Aldrich consisting of 1 mM phenyl methyl sulphonyl fluoride, 5 mM benzamide and 10 mM N-ethylmaleimide at pH 7.4.

The extraction mixture was rocked at 4° C. for 24 h and then centrifuged at 12,000 g (Beckman Coulter) for 30 min at 4° C. Supernatants were collected and 6 mL of freshly prepared urea-heparin extraction buffer was added to each pellet. Pellets with extraction buffer were again shaken at 4° C., centrifuged at 12,000 g for 30 min at 4° C. and supernatants were collected.

Supernatants from first and second extractions were collected and dialyzed with a slide-a-lyzer dialysis cassette 3500 MWCO (Pierce, Rockford, Ill.) against deionized $H_2O$ for three days. The dialyzed extract was used for growth factor quantification.

Concentrations of basic FGF, and TGF-β in the extracts were determined using the human FGF basic mini ELISA developmental kit (Peprotech, NJ, USA), and Mouse/Rat/Porcine/Canine TGF-beta 1 Quantikine ELISA Kit (R & D systems, Minneapolis, USA) respectively. Each assay for basic FGF, and TGF-β was done in triplicate. Both the assays measured the concentration of each growth factor and did not measure the growth factor activity.

Concentration of chemokines in the dialyzed extracts was determined using the PCYTMG-23K-13PX|MILLIPLEX MAP Porcine Cytokine/Chemokine Magnetic Bead Panel—Immunology Multiplex Assay. Each assay was done in duplicate. Manufacturer instructions were followed for the growth factor and chemokine assay.

Example 5: Preparation of Microspheres

Microspheres containing dCM (MS+dCM) were prepared similar to a process described by Sutherland et al. 10 mg dCM powder were solubilized in 10% w/w pepsin (Sigma-Aldrich) in 0.1M HCl solution for 24 h. After the solubilization period, the pH of the solution was raised by adding 1M NaOH and one-tenth the final solution volume of 10×PBS (pH 8). Thereafter, 10 mL of pepsin digested dCM was added to 1500 mg PLA already dissolved in 30 mL dichloromethane (Sigma-Aldrich). Both solutions were mixed and emulsified by using an ultrasonic processor (Qsonica Sonicators Q55, Newtown, Conn. USA) for 60 s in an ice bath, amplitude: 30% for 3 min.

The primary emulsion was added dropwise using a syringe pump (KD Scientific) at the rate of 2.5 mL/min to 300 mL of ice-cold 4% (w/v) polyvinyl alcohol (PVA, Sigma-Aldrich, MW: 13-23 kDa, 87-89% hydrolyzed) solution while mixing by a magnetic stirrer at 700 rpm at room temperature forming a double emulsion. 100 mL of 1% (w/v) PVA solution was then added and the resultant solution was mechanically stirred for 4 h to evaporate the organic solvent at 37° C.

Blank PLA microspheres designated as MS(−) were prepared in a similar way but without addition of dCM. The microspheres were collected by centrifugation at 3500 rpm for 3 min and washed three times with $diH_2O$, lyophilized, separated selectively using sieves (Fisherbrand U.S. Standard Stainless Steel Sieves) into the following size ranges: <53 μm; 53-106 μm and 106-150 μm to optimize release of encapsulated proteins.

Example 6 Characterization of the Prepared Microspheres

Surface Morphology of the Microspheres

The shape and surface morphology of the microspheres was studied by using scanning electron micro-scope (SEM, Hitachi, USA). Lyophilized MS+dCM and MS(−) were mounted onto the SEM sample stub using double-sided sticking tape and sputter-coated with gold-palladium in argon atmosphere using a leica sputter coater to a thickness of 4 nm. The microspheres were then imaged using a 10 kV accelerating voltage and a 10 mm working distance.

Protein Loading and Encapsulation Efficiency (% EE)

The EE % of the microspheres was calculated according to Luciani et al., 2008, PCL microspheres based functional scaffolds by bottom-up approach with predefined microstructural properties and release profiles, *Biomaterials* 29:4800-07.

The dried microspheres (10 mg) were dissolved in 1 mL of dichloromethane. The volume was then adjusted up to 10 mL with methanol for the precipitation of the polymer followed by centrifugation at 15,000 rpm for 15 min. A suitable amount of the supernatant was diluted with distilled water and the absorbance was measured spectrophotometrically at 259 nm. Experiments were carried out in triplicates.

The actual protein loading content (APLC %), theoretical protein loading content, (TPLC %) and the protein encapsulation efficiency (EE %) of PLA MS+dCM was calculated by the following equations as published previously. APLC (%)=(amount of dCM in microspheres/amount of MS+dCM)*100%; TPLC (%)=(amount of dCM used for encapsulation/amount of dCM+polymer used)*100%; % EE=(APLC/TPLC)*100. See, Feng T, et al., 2014, Synergistic co-delivery of doxorubicin and paclitaxel by porous PLGA microspheres for pulmonary inhalation treatment, *Eur. J. Pharm. Biopharm.* 88: 1086-93.

In Vitro Protein Release from Microspheres

In vitro protein release study from microspheres was performed similar to another study. See, Wei Y, et al., 2011, mPEG-PLA microspheres with narrow size distribution increase the controlled release effect of recombinant human growth hormone, *J. Mater. Chem.* 21: 12691-99.

Twenty mg of dried MS+dCM and MS(−) were placed in Eppendorf tubes and suspended in 1 mL of phosphate buffer saline (PBS), pH 7.4 in a 37° C. incubator under mild agitation for 4 weeks.

At appropriate intervals (1, 7, 14, 21, 28 days), the samples were centrifuged for 12 min at 4000 g. The supernatant was withdrawn for protein release assay (n=3) and replaced by fresh PBS. Protein concentration in the release medium was determined by the total protein assay kit as described above (n=3).

Example 7: Cell Culture

Human bone marrow mesenchymal stem cells (hMSCs) were procured from American Type Culture Collection (ATCC) and grown in a humidified chamber at 37° C. and 5% $CO_2$. The adherent cell population was cultured in basal media (BM) consisting of low glucose Dulbecco's Modified Eagle Medium (Life Technologies) supplemented with 10% FBS, 1% penicillin/streptomycin and 1% L-glutamine until reaching sub-confluence, and expanded into a T75 Nunclon™ flask until passage 2.

Example 8: Viability and Adhesion Assay

The viability of hMSCs cultured on MS+dCM and MS(−) was examined using a Live/Dead viability/cytotoxicity kit (Invitrogen). Approximately 10 mg of the spheres were sterilized by 70% ethanol for 1 h. The microspheres were then rinsed with PBS (pH 7.4) repeatedly. Thereafter, PBS was discarded and the cell suspension, containing $1.0 \times 10^5$ cells, was seeded onto the microspheres.

After 7 days, the adherent cells were washed gently with 500-1000 volumes of Dulbecco's PBS and stained with 2 μM calcein AM-4 μM EthD-1 solution for 30 mins, washed and observed under a confocal microscope (Nikon A1Rsi inverted, Japan). Calcein stains the cytoplasm of viable cells green, and an ethidium homodimer stains the nuclei of nonviable cells red. Proliferation of the cells in presence of the microspheres was determined using MTS cell proliferation assay kit using manufacturer's protocol.

The cytoskeleton of hMSCs ($1.0 \times 10^5$ cells) grown on microspheres after 7 days were analyzed using TRITC-conjugated phalloidin-DAPI (Millipore). The cells were fixed in 4% formaldehyde in PBS, permeabilised (0.1% Triton X-100 in PBS) and blocked with 1% BSA in 1×PBS for 30 mins.

The cells were then stained with TRITC-conjugated phalloidin (1:1000) to enable labelling of actin filaments. Those cells were then counterstained with DAPI to visualize the nucleus (1:1000 dilution of a 1 mg/ml stock). Images were taken using a confocal laser scanning microscope. The cells on MS(−) and MS+dCM were also imaged using SEM. After 7 days, the cells were fixed with 2.5% glutaraldehyde for 30 min, washed in deionized $H_2O$, dehydrated in a gradient of alcohol and imaged.

Example 9: Migration Assay

The capability of hMSCs to migrate upon chemotactic stimulation from MS+dCM was assessed using polycarbonate Transwell filters (6.5-mm diameter, 0.8 μm pore size, Corning B.V. Life Sciences, Schiphol-Rijk, The Netherlands) according to a previously published report. See, Ponte et al., 2007 The in vitro migration capacity of human bone marrow mesenchymal stem cells: comparison of chemokine and growth factor chemotactic activities, Stem Cells 25 1737-45.

Prior to the start of experiment, the 24 well plates were filled with 10 mg either MS+dCM or MS(−) in 600 μL serum free basal media (BM). The hMSCs were washed with PBS twice and serum starved for 24 h for synchronization. They were then trypsinised with 0.25% trypsin-EDTA, neutralized with trypsin inhibitor and centrifuged at 200 g for 5 minutes to obtain cell pellets. The pellets were suspended in BM and aliquots of $1 \times 10^5$ cells were plated on the upper chambers of transwells filled with 100 μL BM.

The transwells containing cells were then submerged on 24 wells plates. Transwells containing cells were also submerged in 24 well plates with no microspheres filled with serum containing media/BM served as positive/negative control. After 12 h, the cells in the transwell were fixed with formaldehyde (3.7% in PBS) for 10 mins, permeabilized with 100% methanol for 20 mins and stained with 0.1% crystal violet for 15 mins.

The stain was removed, washed twice with PBS and the non-migrated cells were scraped off from the upper chamber of the transwell with cotton swabs. The cells that migrated to the lower chamber were then imaged using a light microscopy. Data was expressed as percentages of cells related to that of the negative control.

Example 10: Chondrogenic Differentiation

Chondrogenic differentiation was performed according to a previously published study. Approximately, $2 \times 10^5$ cells were centrifuged at 1500 rpm for 5 min in 15 mL falcon tubes to form cell pellets. The pellets were maintained at 37° C. with 5% $CO_2$ in basal media for 24 h, following which they were put in transwell plates placed in 24 well plates.

The 24 well plates contained either MS(−) or MS+dCM. Half of the 24 well plates containing MS(−) or MS+dCM were nourished with BM and other half with chondrogenic induction media (CIM). The CIM consisted of StemPro® Chondrogenesis Differentiation kit (Gibco) containing Basal Medium supplemented with Chondrogenesis Supplement. The medium was replenished every 3rd day for 3 weeks.

Chondrogenesis was evaluated after 21 days qualitatively as well as quantitatively via DNA, collagen, sGAG quantifications (n=3), and real-time polymerase chain reaction (qRT-PCR) (n=6).

Example 11: Histology and Immunohistochemistry

The cell pellets (n=2 per time point of 21 days) were fixed in 4% paraformaldehyde overnight room temperature, embedded in paraffin, cut into 5-mm-thick sections, and mounted on SuperFrost microscope slides (Microm International AG, Volketswil, Switzerland). Sections were deparaffinized, hydrated and stained with toluidine blue to visualize sGAGs deposition.

Immunohistochemistry Sections for immunocytochemistry were deparaffinized and rehydrated followed by washing with PBS. The sections were then covered with pepsin solution (Thermo Scientific) at 37° C., 10 mins for antigen retrieval to expose the epitopes. The sections were allowed to cool at room temperature, washed twice with PBST 20, followed by incubation with 10% normal goat serum (Thermo Fisher Scientific) for 30 minutes to block unspecific binding of the antibodies.

The samples were then incubated with primary antibody Col I (rabbit anti-col I, abcam, ab34710, 1:1000) and COL II (rabbit anti-col II, abcam, ab34712, 1:50) prepared in 1% BSA overnight at 4° C. Cells were washed and incubated with goat anti-rabbit conjugated secondary antibodies, washed and reacted with diaminobenzidine chromogen (Dako) for 10 min and mounted. Samples were imaged using light microscope.

Example 12: Biochemical Analysis

After 21 days, CIM was aspirated and the cells were washed with PBS. The amount of sulfated glycosaminoglycan (sGAG) accumulation was determined using blyscan glycosaminoglycan assay (Biocolor, UK) from the MSCs-pellets (n=3 each) and concentration was calculated from the standard curve. Collagen was also quantified from Hydroxyproline Assay kit (Sigma) following manufacturer's instructions. The amount of sGAG and collagen was normalized to DNA content obtained using a Qubit dsDNA BR assay kit (molecular probes).

Example 13: RNA Isolation and Real Time PCR Studies

RNA was extracted from hMSC pellets at day 21 of differentiation using Trizol reagent (Life Technologies, USA) following the manufacturer's instructions. RNA concentration and quality was determined by a NanoDrop spectrophotometer (Thermo Scientific). Real time PCR studies were performed according to a previous published report. See, Kim C. et al, 2016, Local delivery of a carbohydrate analog for reducing arthritic inflammation and rebuilding cartilage, *Biomaterials* 83: 93-101.

RNA (1 µg) was treated with DNAse I to remove potential genomic DNA contamination and then reverse transcribed with the Superscript II reverse transcriptase kit (Invitrogen, 18064-014, USA) following the manufacturer's protocol. Resulting cDNA (~20 µL) was diluted to 180 µL with dH$_2$O to give a final concentration of approximately 10 ng/mL cDNA. Real-time Polymerase Chain Reaction (PCR) was performed using StepOnePlus Real Time PCR System (Applied Biosystems, USA) with SYBR Green PCR Master Mix (Life Technologies, USA). The sample that did not contain transcription enzyme was used as negative control to check for genomic DNA contamination.

Expression levels of each gene were calculated from data obtained using the $2^{-\Delta\Delta CT}$ method where actin was used as endogenous control and the MSc aggregate sample at day 1 was set as the calibrator.

Example 14: Production of Microspheres Encapsulating Alkaline Phosphatase

Alkaline phosphatase (ALP, Sigma) was used as a surrogate for dCM in order to assess functional integrity of the microspheres and filaments after fabrication process. ALP was diluted in the ratio 1:1000 in Tris-HCl buffer, pH 8 containing 5 mM MgCl$_2$.H$_2$O and incorporated in PLA microspheres via double emulsion technique as described above (MS+ALP).

Example 15: Production of Filaments

Production of Filaments Containing Microspheres

MS(−) and MS+ALP were mixed via a rolling mixer with polycaprolactone (PCL, MW≈50,000, Perstorp, USA) to a final weight ratio of 20:80; the mixture was then added to a custom extruder set at 57° C. and pulled with constant tension to produce a 1.75 mm diameter filament via melt extrusion. PCL-only filaments to be used as controls were produced in a similar manner without mixing with microspheres.

The filaments were stored at −80° C. until further use. Specimens were analyzed for surface features using SEM.
Functional Assay for Filaments Eighty mg MS(−), 80 mg MS+ALP, 400 mg filament with MS+ALP, 400 mg filament with MS(−), and 400 mg PCL-only filament were weighed, put in centrifuge tubes containing 1 mL Tris-HCl and incubated in shaker for 24 h at 37° C., 110 rpm following which 1 mg substrate p-nitrophenyl phosphate, disodium hexahydrate (Sigma) dissolved in 1 mL Tris-HCL was added so that final concentration of the substrate was 0.5 mg/mL (1.35 mM).

The resulting mixture was again incubated at 37° C., 110 rpm for 10 h and absorbance was read at 415 nm. Experiments were repeated in triplicate and average value was determined.

TABLE 1

Gene Primer Sequences Used for Quantitative, Real-Time PCR

| Primer | Fwd | SEQ ID | Rev | SEQ ID |
|---|---|---|---|---|
| ACAN | TGGGAACCAGCCTATACCCCAG | SEQ ID NO: 1 | CAGTTGCAGAAGGGCCTTCTGTAC | SEQ ID NO: 2 |
| SOX9 | GCATGAGCGAGGTGCACTC | SEQ ID NO: 3 | TCTCGCTTCAGGTCAGCCTTG | SEQ ID NO: 4 |
| COL II | CGCCGCTGTCCTTCGGTGTC | SEQ ID NO: 5 | AGGGCTCCGGCTTCCACACAT | SEQ ID NO: 6 |
| COL I | GAATGCCTGGTGAACGTGGT | SEQ ID NO: 7 | AGGAGAGCCATCAGCACCTTT | SEQ ID NO: 8 |
| COL X | TGCTGCCACAAATACCCTTT | SEQ ID NO: 9 | GTCGACCAGGAGTACCTTGC | SEQ ID NO: 10 |
| OCN | GTGACGAGTTGGCTGACC | SEQ ID NO: 11 | TGGAGAGGAGCAGAACTGG | SEQ ID NO: 12 |
| RUNX2 | CTTCACAAATCCTCCCAGTAGCTA | SEQ ID NO: 13 | GGTTTAGAGTCATCAAGCTTCTGTCT | SEQ ID NO: 14 |
| ACTIN | TGAAGGTCGGAGTCAACGGATTTGGT | SEQ ID NO: 15 | CATGTGGGCCATGAGGTCCACCAC | SEQ ID NO: 16 |

Example 16: Statistical Analysis

Statistical analysis was done in Graphpad Prism, version 5. Data was expressed as mean±standard deviation. Unpaired Student's t-test was used to compare two groups.

Example 17: Decellularization

Porcine hind limbs were harvested and subsequently decellularized. FIG. 1a. A reduction in the visible cell nuclei was observed after decellularization using H&E staining. FIG. 1b.

The DNA content of the decellularized tissue was significantly decreased by 98.4% (10.5±1.6 ng DNA/mg tissue dry weight, $p<0.0001$) when compared to the fresh-frozen tissue (650±77 ng DNA/mg tissue dry weight). FIG. 1c.

MT staining revealed the overall preservation of collagen matrix, while alcian blue staining indicated reduction in the sGAG content in the decellularized cartilage compared to native tissues. FIG. 1b. Total protein before and after decellularization was 961.9±33.3 and 861.5±30.1 µg/mg dry weight respectively, ($p<0.05$) indicating 89.6% retention of the proteins. FIG. 1d.

The native tissue was composed of 44.7±4.5 (0.1 µg collagen/mg dry weight, 110.2±3 µg sGAG/mg dry weight while decellularized cartilage contained 33.3±1.7 (0.1 µg collagen/mg dry weight and 68±2.2 (0.1 µg sGAG/mg dry weight indicating retention of 74.5% collagen ($p<0.05$) and 61.82% sGAGs ($p<0.0001$). FIG. 1e and FIG. 1f.

These results show that the decellularization process conserved the ECM components while removing bulk of the DNA material.

Example 18: Growth Factor and Chemokine Quantification

Growth factor analysis indicated 68.8% of bFGF ($p<0.05$) and 42% of TGF β ($p<0.01$) remained in the cartilage tissue after the decellularization process. See, FIG. 2a and FIG. 2b. 3.2±0.25 pg of bFGF per mg dry weight of cartilage was present in native cartilage in comparison to 2.2±0.132 pg of bFGF/mg initial dry weight after decellularization. TGF β was present at levels of 9.04±0.5 pg/mg initial dry weight and 3.8±0.3 pg/mg initial dry weight in native and decellularized cartilage tissue, respectively.

No significant decrease in the amount of cytokines (GM-CSF, IFNγ, IL-1α, IL-1β, IL-1ra, IL-2, IL-4, IL-6, IL-8, IL-10, IL-12, IL-18, TNF-α) was observed after processing of the cartilage tissue. FIG. 2c.

Example 19: Microsphere Formation

Figure 3:
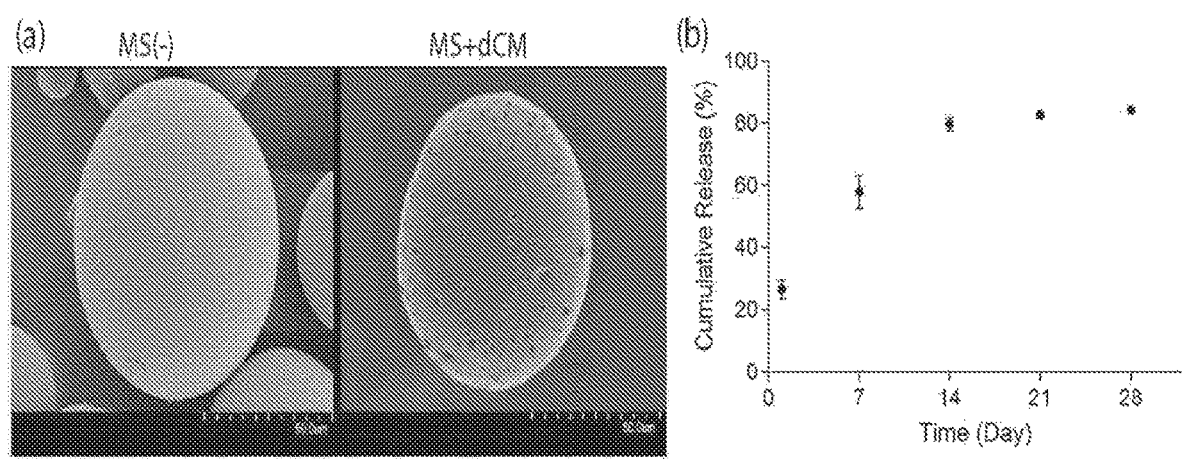
FIG. 3. (a) provides representative SEM images of MS(−) and MS+dCM, scale bar 50 μm; and (b) the Protein release profile from the MS+dCM over 4 weeks. Values are mean±SD. MS(−), blank microspheres; MS+dCM, microspheres containing decellularized chondral matrix.

SEM images of PLA MS(−) and MS+dCM are shown in FIG. 3a. The MS(−) had smooth, even and non-porous surface whereas the MS+dCM showed numerous small pores on the surface. The size range of the microspheres observed after sieving was 50-150 µm. The protein encapsulation efficiency (EE) values determined for MS+dCM was 63.4%.

The cumulative release of proteins from MS+dCM was monitored over 28 days. FIG. 3b. At day 1, 26.6% of the initially loaded protein was released from MS+dCM, followed by a sustained release of the proteins from MS+dCM throughout 4 weeks.

Example 20: Cell Viability and Adhesion

Figure 4:
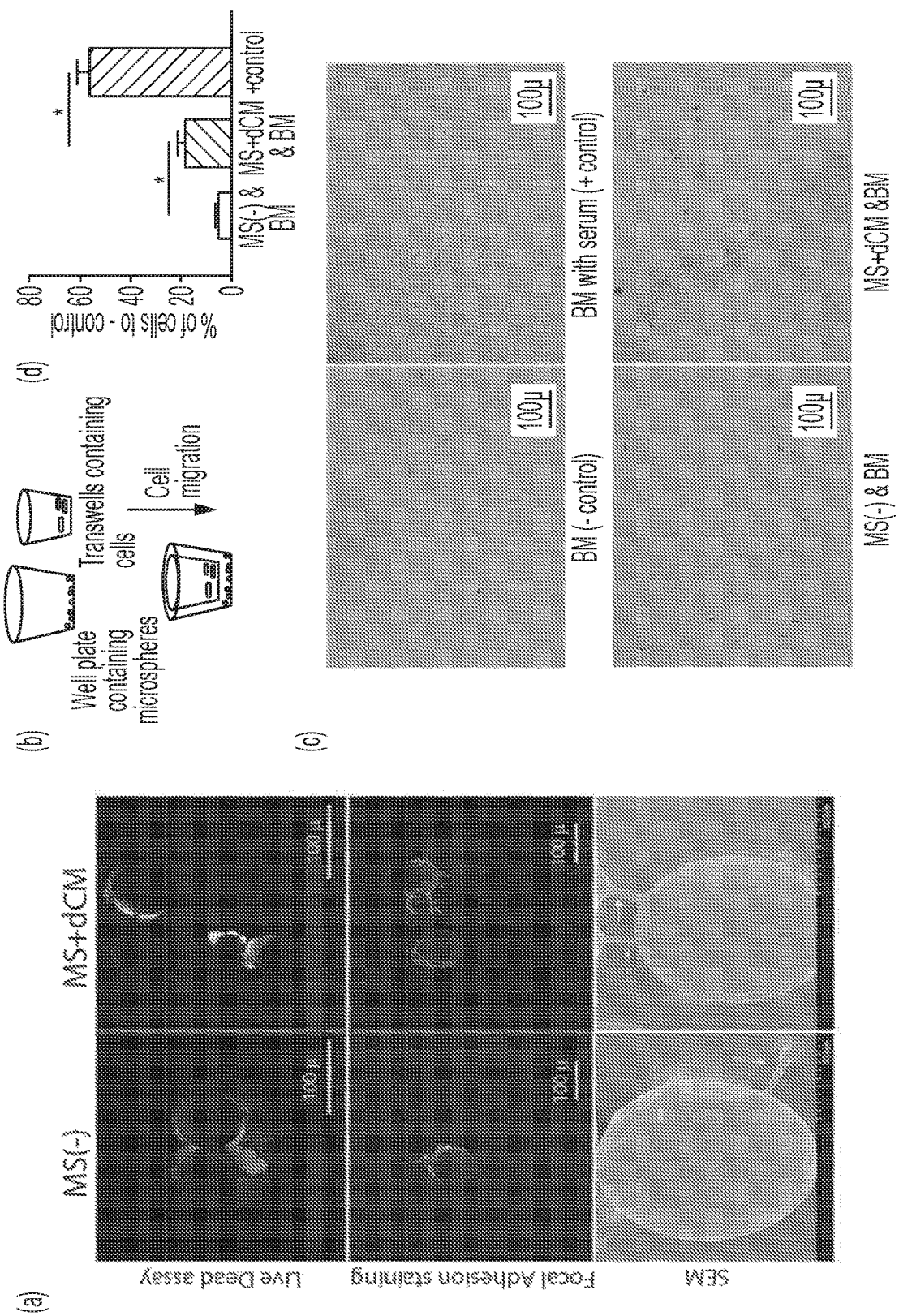
FIG. 4. (a) illustrates results from the live-dead assay to determine the hMSC viability on MS(−) and MS+dCM, scale bar 100μ; TRITC conjugated phalloidin and DAPI to evaluate actin filament morphology of cells on MS(−) and MS+dCM, scale bar 100μ; and SEM to assess cell adhesion on MS(−) and MS+dCM, scale bar 50μ; (b) provides schematic representation of cell migration using Transwell membrane; (c) demonstrates that cells migrated in response to different conditions stained with crystal violet; scale bar 100μ; and (d) provides the migration index for cells cultured in different conditions, normalized against the value for cells migrated in presence of serum free basal media (negative control). Values are mean±SD, (*$p<0.05$). MS(−), blank microspheres; MS+dCM, microspheres containing decellularized chondral matrix.

Confocal microscopy confirmed the existence of viable cells on the surface of the microspheres after culturing for 7 days. FIG. 4a. The round black regions are microspheres, while the green bright regions represent viable hMSCs. The cells tended to attach and grow in the gaps between the microspheres. It can be seen that the cells could grow on all the microspheres, however, the number of viable cells on the MS+dCM was 11% higher than that on the MS(−) after 7 days.

To analyze the effect of MS+dCM on hMSC cytoskeleton, staining with TRITC-conjugated phalloidin was performed. The actin filaments were observed on both the MS(−) as well as MS+dCM indicating that the morphology of the cells were not affected by dCM or poly(lactic) acid. Cell adhesion was also observed in both groups as evidenced from SEM.

Example 21: Migration Assay

A transwell based migration assay was established to quantitatively evaluate hMSC migration in vitro in response to chemical stimulants released from the MS+dCM. FIGS. 4b-4d. The average number of migrated cells were highest for positive control i.e. media with serum and lowest for negative control i.e. basal media (BM) without serum.

There was no statistical difference in the number of migrated cells in negative control group and MS(−) & BM group. Interestingly, the average number of migrated cells was statistically higher ($p>0.05$) in the MS+dCM & BM group in comparison to MS(−) & BM group. This establishes that cells can migrate without serum in presence of MS+dCM supporting the role of chemokines/growth factors released from the MS+dCM as the most likely variable responsible for hMSC migration.

Example 22: Histology and Immunohistochemistry

Figure 5:
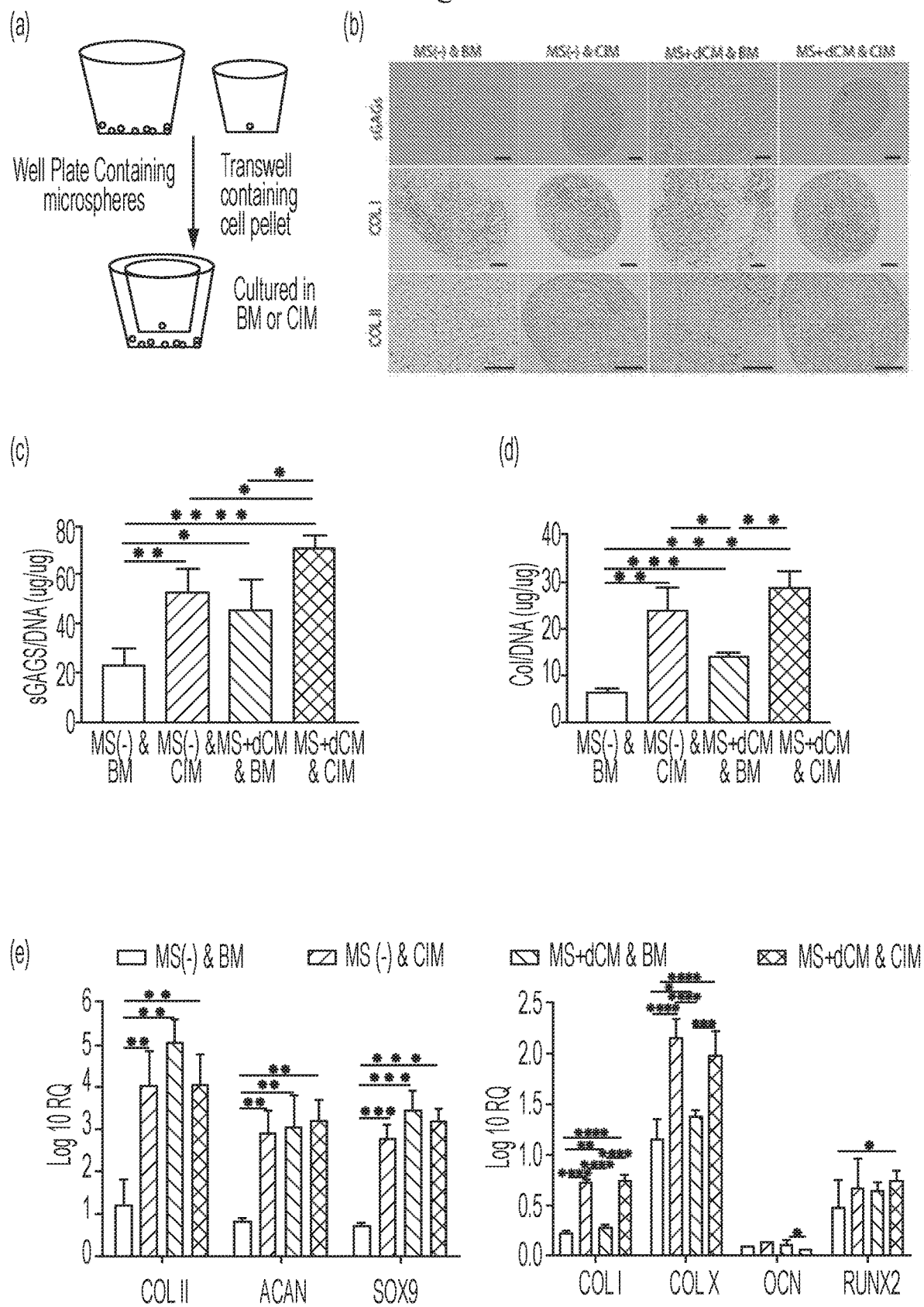
FIG. 5 illustrates the chondrogenic differentiation of hMSCs in vitro, according to one embodiment. (a) provides schematic of cell differentiation. (b) provides comparison of deposition of sGAGs, COL I and COL II by cell pellets using histology and immunohistochemistry, scale bar 100μ. Original magnification for sGAGs and COL I was 10× and for COL II was 20×. (c) shows quantification of sGAGs and (d)

Significant deposition and accumulation of cartilage matrix components by the differentiating cells within the cell pellets was observed through histological and immunohistochemical staining. FIG. 5. Pellet cultures in basal media (BM) were considerably disorganized.

The cell pellets grown in presence of MS+dCM had more prominent sGAG staining than the cells grown in MS(−) in basal media. The cell aggregate grown in presence of MS+dCM & chondrogenic induction media (CIM) showed the highest sGAG deposition and were well-organized in a high-density, compact structure.

Immunohistochemical staining of Col II was prominent for cell pellets grown in presence of MS+dCM and/or CIM, especially in the inner layers. FIG. 5b. Col II was absent from the cell pellets cultured in presence of MS(−) & BM. Col I was evident on all the cell pellets.

Example 23: Biochemical Analysis

Biochemical analysis of the cell pellets at day 21 demonstrated that the DNA level, a surrogate for cell number, was similar in all the pellets. The amount of sGAG per DNA content significantly increased when pellets were cultured in presence of MS+dCM and/or CIM. FIG. 5c.

For instance, biochemical quantification of cell pellets cultured in presence of MS(−) & CIM (52.6±9.9 µg/µg, $p<0.01$), MS+dCM & BM (45.6±12.4 µg/µg, $p<0.05$) and MS+dCM & CIM (70.5±5.5 µg/µg, $p<0.0001$) showed higher deposition of sGAGs/DNA compared to the pellets cultured in presence of MS(−) & BM (22.8±7.2 µg/µg sGAG/DNA) at day 21.

Similarly, COL/DNA value of the cell pellets when cultured in presence of MS(−) & CIM, MS+dCM & BM and MS+dCM & CIM were 23.8±5 (p<0.01), 14.2±0.8 (p<0.001) and 28.9±3.5 (p<0.001) µg/µg respectively, compared to 6.4±0.8 µg/µg Col/DNA for MS(−) & BM. FIG. 5d.

These results demonstrate that sustained delivery of cartilage-specific proteins released from the MS+dCM provide inductive cues for differentiation of progenitor cells without the need for traditional cartilage induction medium, which classically requires exogenous supplementary factors.

Example 24: Gene Expression Analysis

Expression of previously identified key cartilage matrix, hypertrophy and osteogenic genes were analyzed by qPCR and data were compared between hMSCs pellets cultured in presence of microspheres with or without chondrogenic induction media after 21 days. FIG. 5e.

Expression of COL II, ACAN and SOX 9 increased by more than 3-fold in the hMSCs pellets cultured in presence of MS(−) & CIM, MS+dCM & BM and MS+dCM & CIM compared to MS(−) & BM (p<0.01).

No statistically significant differences were observed between MS(−) & CIM, MS+dCM & BM and MS+dCM & CIM expression levels for the above genes. This indicates that sustained delivery of proteins from MS+dCM in absence of chondrogenic induction medium can enhance the expression of markers of chondrogenesis at a similar level as that seen after exposure of hMSCs to traditional chondrogenic media.

Interestingly, COL I and COL X transcript expression was an order or less in magnitude when the pellets were cultured in presence of MS+dCM & BM than cultured in presence of MS+dCM & CIM (p<0.001). FIG. 5e. This indicates that sustained delivery of proteins from MS+dCM in absence of chondrogenic induction medium can reduce the expression of known hypertrophy related markers previously associated with dedifferentiation of chondrocytes and resultant endochondral ossification.

OCN expression was low for all conditions indicating that the osteogenic genes were weekly expressed in all of the cell pellets. RUNX 2 expression was also similar for all the conditions.

Example 25: Extrusion of PCL Filaments Containing Microspheres

PCL filaments of 1.75 mm diameter containing MS+ALP and MS(−) were successfully drawn by melt extrusion. FIG. 6a. SEM of a representative filament containing microspheres is shown in FIG. 6b and FIG. 6c. Filaments without microspheres were also produced and used as control.

Example 26: Functional Assay for Filaments

Enzyme alkaline phosphatase (ALP) was used as a surrogate to study encapsulated protein functionality after microsphere incorporation and filament production. FIG. 7. Microspheres and filaments were incubated in Tris-HCL buffer for 24 h so that enzyme diffusion could occur.

When the colorless substrate p-nitrophenyl phosphate was added to the buffer after 24 h, the color changed to yellow for the MS+ALP, while the MS(−) did not depict any appreciable color change. FIG. 8. The absorbance values for MS+ALP and MS(−) were 0.235±0.005 and 0.1±0.003 respectively (p<0.05). This is because ALP that diffused out from the MS+ALP hydrolyzes the substrate to produce a yellow-colored product, p-nitrophenol and inorganic phosphate. Similarly, MS+ALP in filaments (0.145±0.017) had significantly (p<0.05) higher absorbance value than MS(−) in filaments (0.081±0.006) and PCL only filaments (0.097±0.005).

Example 27: Decellularized Cartilage Matrix Encapsulated in 3D Printed Scaffolds for Large Osteochondral Repair Promotes Cell Viability and Attachment Donor porcine cartilage was decellularized and encapsulated in polylactic acid (PLA) microspheres as previously described. The decellularized matrix (DM) microspheres were co-extruded with polycaprolactone (PCL) powder at a weight ratio of 1:4 to create filament [PLA-DM/PCL] for a commercially available desktop 3D printer.

Filament with blank microspheres [PLA(−)/PCL] and filament without microspheres [PCL(−)] was also produced. Scaffolds from each filament type were printed with a 0°, 60°, and 120° laydown pattern with approximately 400 µm strut and pore size. Compressive Young's moduli were measured in phosphate buffered saline according to ISO 13781 (n=5). Subsequently, the scaffolds (n=3) were sterilized and seeded in basal media (BM) with 2×10⁵ cells/scaffold.

After the third day after seeding, half of the scaffolds for biochemical analyses were cultured in chondrogenic media (CM, n=3). BM or CM was changed every 2-3 days for 28 days. At 28 days, BM cultured scaffolds were stained with calcein/ethidium homodimer via live/dead kit, DAPI/TRITC/FITC via actin cytoskeleton and focal adhesion kit to stain nuclei and focal adhesion points, and fixed and processed for scanning electron micrography. DNA content and collagen content normalized to DNA was assessed for both BM and CM cultured scaffolds after 28 days. When applicable, groups were compared via one-way ANOVA with Tukey's post-hoc test (p<0.05 significant).

The Young's modulus for the PCL(−) and PLA-DM/PCL groups was 0.3869±0.0725 MPa and 0.4482±0.0375 MPa respectively, with the addition of DM and microspheres not contributing to any significant difference. FIG. 8.

FIG. 9a shows that viable cells were present on each of the scaffolds throughout the culture period. Focal adhesion staining shows that cells were homogenously attached on PCL(−) and PLA(−)/PCL scaffolds, and clustered on the PLA-DM/PCL scaffolds after day 21. FIG. 9b. SEM showed cells attached on the surface and extracellular matrix deposited throughout all scaffold groups. FIG. 9c.

FIG. 10 shows results from biochemical analyses, with significant differences in DNA content between the PLA-DM/PCL in CM group and other CM groups, and no significant difference in estimated collagen content between groups. Other significant differences in estimated DNA content are marked by lines in FIG. 10a.

The addition of microspheres did not significantly impact the modulus of elasticity of the scaffolds and allowed mimicry of native chondral tissue. The addition of DM to the scaffolds caused cells to cluster, which is promising as an initial indicator of chondrocyte condensation. Over 28 days, cells attached and laid extracellular matrix on the scaffolds. There were significant differences in the DNA content of PLA-DM/PCL in CM which may indicate early differentiation of the hMSCs and a subsequently lower rate of proliferation. However, there was no significant difference in hydroxyproline content between cells on different scaffolds with CM and BM which may be due to high variability in the hydroxyproline readings.

The treatment option in this study has the potential to improve outcomes for pediatric populations with large OCI and reduce the need for premature joint replacement. Based on the flexibility of the production technique and the ability to harvest and decellularize donor tissue from any organ type, the scaffold manufacturing technique explored in this study also has potential for treatment of many other pathologies that are good candidates for tissue engineering such as bone, craniofacial, and other structural tissue repair.

Example 28: Microspheres Containing Decellularized Cartilage Induce Chondrogenesis In Vitro and Remain Functional after Incorporation within a Poly(Caprolactone) Filament Useful for Fabricating a 3D Scaffold Alkaline phosphatase (ALP) was encapsulated in microspheres and printed within polycaprolactone (PCL) filament, PLA-ALP/PCL, as an easy approximation of protein damage during the printing process.

ALP remained functional after the printing process, as evidenced by its catalysis of the colorimeteric reaction from p-nitrophenyl phosphate to p-nitrophenol and inorganic phosphate. *=sig difference ($p<0.05$) from all but 2 PLA (−)/PCL, =sig difference ($p<0.01$) from all other groups, *=sig difference from all other groups ($p<0.01$). FIG. 11. Decellularized cartilage matrix (DM) contained in microspheres and DM contained in printed scaffolds both showed sustained release of matrix proteins (via Lowry Assay) over the 8 week period. FIG. 12. It is likely that the higher surface area of the microspheres led to faster DM release than in that of the 3D printed scaffolds.

The 3D printed scaffolds were seeded with $2\times10^5$ human mesenchymal stem cells (hMSCs). They were cultured over 28 days in basal media. They were stained with kits for live/dead cells and focal adhesion and fixed and coated for scanning electron microscopy (SEM). The live/dead panel shows that the scaffolds had good viability. The focal adhesion assay shows clustering of cells that was typical for the PLA-DM/PCL scaffolds after day 21 of culture. This behavior, called condensation, is characteristic of progenitor cells undergoing cartilaginous differentiation. SEM images show extracellular matrix deposition in all of the scaffold groups. Microspheres can also be observed in the PLA-DM/PCL and PLA(−)/PCL groups with hMSCs attached on and around them. FIGS. 9a-c.

Biochemical assays to determine DNA and hydroxyproline content, which is an indicator of collagen deposition, were similarly carried out after seeding with $2\times10^5$ hMSCs/scaffold and culturing with both basal media (BM) and chondrogenic media (CM) after 28 days. DNA concentration in the PLA-DM/PCL scaffolds in CM was significantly lower than that of PLA(−)/PCL and PCL(−) in CM and PLA(−)/PCL in BM. PCL(−) in CM had significantly higher DNA than PLA-DM/PCL and PCL(−) in BM. It is hypothesized that the DNA is decreased in the DM containing samples because the release of DM proteins and growth factors induces immediate chondrogenesis and that after initiation of differentiation, proliferation plateaus. Hydroxyproline content (normalized to DNA) of the PLA-DM/PCL samples is increased from the other scaffold groups in both basal media and chondrogenic media, although not statistically significantly. FIG. 10a and FIG. 10b.

Example 29: 3D Printing with Decellularized Extracellular Matrix for Osteochondral Repair Decellularized extracellular matrix (DM) contained within a thermally protective PLA barrier can be printed within PCL filament and remain in its functional conformation.

Porcine cartilage matrix was harvested post-sacrifice and decellularized via a series of rinses and washes using the methods described herein. The cartilage decellularized matrix (DM) was encapsulated in PLA via emulsification. The microspheres [PLA-DM] were then extruded with PCL powder to produce filament for 3D printing.

The filament was used to make porous scaffolds via fused deposition modeling using a 400 micron nozzle at 70° C. In addition to the experimental group which contained DM microspheres [PDA-DM/PCL], two control groups were printed: PCL only scaffolds [PCL(−)] and PCL scaffolds with blank microspheres [PLA(−)/PCL]. The scaffolds were analyzed for surface features via scanning electron microscopy (SEM).

Total in vitro protein release from the scaffolds placed in PBS was tested via Lowry assay, Onishi & Barr Modification, over an 8 week period.

Alkaline phosphatase (ALP) was encapsulated in microspheres and printed into scaffolds as described above. The ALP was uses as a surrogate to test post-printing functionality of the enzyme, and therefore the expectation of maintaining functional extracellular matrix proteins when printing with DM.

Groups were compared via one-way ANOVA with Tukey's post-hoc test when applicable (n=3 for all experiments). The results shown in FIG. 11 and FIG. 12 demonstrate that the PCL scaffolds with incorporated dCM microspheres can produce prolonged release of matrix proteins that remain in their functional, non-denatured conformation.

Example 30: Process for 3D Printing Decellularized Matrices Protocol

Obtaining Microspheres and Microsphere Preprocessing 1.1: Obtain microspheres with the desired matrix encapsulated, PLA-DM, by following a protocol that has been previously reported. It is important that the microspheres are of uniform size. For this reason, the microspheres are sieved prior to use. The process is as follows.

1.1.1: First, cartilage plugs are harvested from porcine hind limbs. The cartilage is decellularized in a series of washes with 0.05% trypsin/0.5 mm tetrasodium EDTA, Dulbecco's modified Eagle's medium (DMEM), and peracetic acid and 2.0% Triton X-100 for 4 hours each with distilled water washes before and after each step.

1.1.2: The decellularized matrix is drained, frozen, lyophilized and ground, and dissolved into pepsin solution. Following dissolution, the pepsin solution is mixed with PLA which has been dissolved in dichloromethane. The mixture is then added dropwise into a 3% polyvinyl alcohol in water solution. The resulting microspheres are centrifuged, rinsed, drained, and lyophilized again.

1.2: Sieve microspheres 1.2.1: Ensure that all sieve plates have been thoroughly cleaned and are dry prior to use.

1.2.1.1: If necessary, clean sieves using ultrasonic cleaner to ensure that all spheres are removed from the sieve.

1.2.2: Assemble the sieve shaker with the 106 μm sieve tray at the top, 53 μm tray after that, and the sieve pan at the bottom.

1.2.3: Place dry microspheres in the top sieve tray and place the lid on the top tray.

1.2.4: Turn on coarse sieving for 8 to 10 minutes. Repeat on fine for 8 to 10 minutes. The sieve times may need to increase or decrease depending on the batch.

1.2.5: Carefully remove sieve plates one by one and place upside down on large weigh paper. Tap sides gently to ensure that most of the spheres have fallen out of sieve and onto the paper.
1.2.6: Discard the oversized spheres (>106 μm) and undersized spheres (<53 μm). Add spheres that are in the 53-106 μm size range to a labeled centrifuge tube with type and batch number then place in −20° C. freezer until further use.

Microsphere Quality Control Assessments 2.1: Macroscopic/visual assessment.
2.2: Microspheres should be uniform and spherical, with no aggregates present.
2.3: Scanning electron micrograph (SEM).
2.4: Place microspheres onto an SEM chuck and sputter coat with gold-palladium in argon atmosphere using a sputter coater to a thickness of 4 nm. Observe surface features, morphology, and diameter of the microspheres using a 10 kV accelerating voltage and a 10 mm working distance to ensure production and sieving of the microspheres was successful.

Creating Filament for 3D Printing 3.1: Measure and record mass of microspheres obtained from steps 2 and 3. At least 25 grams is needed.
3.2: Add polycaprolactone (PCL) powder to the microspheres for a 1:4 weight ratio of microspheres to PCL.
3.3: Mix the powder mixture on a miniature rolling mixer at 20 RPM for 5 minutes then flip the container and mix at 20 RPM for an additional 5 minutes.
3.4: Modify extruder (if necessary)
3.4.1: Many commercially available extruders have insulating jackets because their intended working temperatures are for traditional FDM filaments. Removal of the insulating material in combination with desktop fans which blow ambient air onto the extruder and extruded filament enables use of the extruder at lower temperatures.
3.5: Equipment setup for extrusion
3.5.1: The outlet of the extruder should be approximately 60 cm from the inlet to the spooler, with a direct path from the extrusion outlet to the spooler inlet. The spooler can optionally be raised 3-4 inches from the bench if it is found that the filament is drooping to the point of touching the benchtop.
3.5.2: Desktop fans that blow ambient air to cool the extruder and filament are useful for this procedure. A desktop fan can be placed approximately 15 cm from the heating jacket and directed toward the heating jacket to offer cooling with ambient air throughout filament production. A second cooling fan can be placed approximately halfway between the extruder and spooler and directed toward the extrudate to assist in cooling the filament with ambient air.
3.5.3: Adjust the positioning as needed throughout the process.
3.6: Set the modified extruder heating element to 52° C., turn on the desktop cooling fans, and allow the instrument to come to equilibrium for 20 to 30 minutes. Ensure the proper nozzle is attached to the extruder.
3.7: Just before beginning, fill the extruder hopper with the microsphere/PCL mixture from step 3.3. Turn on the spooler and the extruder auger to initiate extrusion of filament.
3.8: When the initial filament is extruded, manually pull the extrudate from the extrusion outlet with forceps and feed it to the filament spooler (Filabot).
3.9: The desired filament will take some time to come out of the spooler. Clearly mark using separate spools or tape when the filament composition visually appears uniform.
3.10: Monitor the process closely and modify parameters as necessary. Close attention is required during this process to obtain adequate filament for subsequent 3D printing.
3.10.1: Adjust the extruder temperature, extrusion auger speed, and spooler speed to attain 1.75 mm diameter filament as measured by caliper. Adjustment of the fans may be needed to cool the filament properly to avoid non-circular filament cross-sections. These parameters will change depending on the ambient conditions, the fill level and uniformity of the mixture in the hopper, and the thermodynamics and flow dynamics of the specific batches of PCL and microspheres.
3.10.2: Mix and refill the hopper as necessary.
3.11: Continue extruding until all of the powder has been used and the hopper is almost empty.
3.12: Add PCL powder (without microspheres) to the hopper to flush out the microsphere mixture that is currently in the extruder. Continue adding PCL powder to the hopper until no more microspheres are visible in the extrudate. Be sure to label and separate the filament which contains the microspheres in the desired concentration, as after the filament is cooled it is harder to distinguish the uniform filament from non-uniform filament.
3.13: Continue extruding until there is minimal powder left in the hopper, then turn off the spooler, extruder auger, extruder heating element, and fans.

Printing with the Filament 4.1: Design a geometry of the desired shape and form using a computer aided design software. Slice the model and dictate the toolpath using slicing software that is compatible with the 3D printing machine being used.
4.2: Load the filament from steps 3.7-3.9 to any standard fused deposition modeling printer, fitted with standard nozzles of the desired diameter (typically 0.4 mm). Begin the print (typically at 65-70° C. and 300 mm/min linear speed) as the custom filament is deposited layer-by-layer by the machine. Make sure to pay special attention to the first layer and adjust as needed to get a good quality print. Adjustments may be made to the print speed, print temperature, platform temperature, extrusion multiplier, and other parameters.

Quality Control Assessment 5.1: Scanning electron micrograph
5.1.1: Place the printed constructs on SEM chucks and sputter coat with gold-palladium in argon atmosphere using a sputter coater to a thickness of 4 nm. Observe under the microscope using a 10 kV accelerating voltage and a 10 mm working distance for surface features and presence or absence of microspheres if applicable.

Functional Testing of the Printed Constructs 6.1: Alkaline phosphatase (ALP) can be used as a surrogate for decellularized matrix to determine if encapsulated proteins are biologically active after the filament production process. ALP is used because it catalyzes a reaction from a substrate, p-nitrophenyl phosphate, to change from colorless to yellow byproducts, p-nitrophenol and inorganic phosphate, but only if ALP is in the functional conformation.
6.1.1: Print a geometry (n=3) that has an end mass of at least 400 mg with the ALP microsphere filament (PLA- ALP/PCL) using identical print parameters as the PLA-DM/PCL scaffolds. Also print PCL(−) scaffolds of the same geometry as the PLA-ALP/PCL scaffolds. Submerge them in 1 mL Tris-HCl buffer and incubate for 24 hours at 37° C. and 110 rpm to allow enzyme diffusion.

6.1.2: Add 1 mL of 1 mg/mL p-nitrophenyl phosphate, disodium hexahydrate in Tris-HCl. Incubate at 37° C., 110 rpm for an additional 10 hours. Read supernatant absorbance at 415 nm.

After sieving, microspheres appeared uniform and free from aggregates. Under SEM, the sieved microspheres may have small pores on their surface, but are otherwise spherical and smooth. All extruded filaments were of uniform diameter and circular cross-section. Filament that contains microspheres [PLA-DM/PCL] had a slightly more matte finish while PCL only [PCL(−)] filament looked more glossy.

The PLA-DM/PCL filaments feel coarser to the touch than the PCL(−) filaments. Scaffolds are printed in the desired geometry which was dictated by the software in step 4.1. The scaffold quality and shape is repeatable and uniform from one print to another. After printing, macroscopically scaffolds with and without microspheres are difficult to distinguish, but under SEM microspheres are visible on the surface and throughout the constructs.

Under SEM, PCL(−) filament appeared smooth, with some striations as an artifact of the extrusion process. Microspheres were visible both protruding through and under the surface of the PLA-DM/PCL scaffolds. When using ALP as a surrogate for DM, the functionality of the enzyme within the scaffold was maintained with significantly higher absorbance ($p<0.05$) at 415 nm than those of blank PCL(−) scaffolds, 0.297±0.023 and 0.166±0.012, respectively.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

Various modifications of the present invention, in addition to those shown and described herein, will be apparent to those skilled in the art of the above description. The following claims, including all equivalents thereof, are intended to define the scope of the invention.

The invention claimed is:

1. A fabricated filament comprising:
   a plurality of decellularized matrix microspheres comprising a first polymer encapsulating a decellularized donor tissue, wherein the first polymer comprises one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, and nylons; and
   a second polymer,
   wherein the decellularized matrix microspheres and the second polymer are co-extruded in the form of the filament.

2. The filament of claim 1, wherein the first polymer comprises polylactic acid (PLA).

3. The filament of claim 1, wherein the donor tissue comprises chondral tissue, tracheal tissue, bone tissue, cardiovascular tissue, nerve tissue, muscle tissue, skin, organ tissue, one or more growth factors, one or more cytokines, or a tissue derived from mesodermal, ectodermal, or mesenchymal origin.

4. The filament of claim 3, wherein the donor tissue comprises chondral tissue.

5. The filament of claim 1, wherein the second polymer comprises one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, and polyamide.

6. The filament of claim 5, wherein the second polymer comprises polycaprolactone (PCL).

7. The filament of claim 1, wherein the plurality of decellularized matrix microspheres and the second polymer are at a weight ratio of about 1:4.

8. A method of manufacturing a filament, the method comprising:
   decellularizing a donor tissue;
   encapsulating the donor tissue in a first polymer to provide decellularized matrix microspheres, wherein the first polymer comprises one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, and nylons; and
   co-extruding the decellularized matrix microspheres with a second polymer to provide the filament.

9. The method of claim 8, wherein the donor tissue comprises chondral tissue, tracheal tissue, bone tissue, cardiovascular tissue, nerve tissue, muscle tissue, skin, organ tissue, one or more growth factors, one or more cytokines, or a tissue derived from mesodermal, ectodermal, or mesenchymal origin.

10. The method of claim 8, wherein the second polymer comprises one or more of polycaprolactone (PCL), polyvinyl acetate (PVAC), ethylene vinyl acetate polymer (EVA), polyvinyl alcohol (PVA), polylactic acid (PLA), polyglycolic acid (PGA), polylactic-co-glycolic acid (PLGA), polyalkyl cyanoacrylate, polyurethane, and polyamide.

* * * * *

UNITED STATES PATENT AND TRADEMARK OFFICE
CERTIFICATE OF CORRECTION

PATENT NO.        : 11,712,496 B2                                    Page 1 of 1
APPLICATION NO.   : 16/759380
DATED             : August 1, 2023
INVENTOR(S)       : Chia-Ying James Lin et al.

It is certified that error appears in the above-identified patent and that said Letters Patent is hereby corrected as shown below:

In the Specification

In Column 15, Line(s) 1, delete "Alter" and insert --After--, therefor.

In Column 15, Line(s) 2, delete "lint" and insert --1mL--, therefor.

Signed and Sealed this
Tenth Day of December, 2024

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: ACAN forward primer

<400> SEQUENCE: 1
tgggaaccag cctatacccc ag        22

<210> SEQ ID NO 2
<211> LENGTH: 24
<212> TYPE: DNA
<213> ORGANISM: Artificial Sequence
<220> FEATURE:
<223> OTHER INFORMATION: ACAN reverse primer

<400> SEQUENCE: 2
cagttgcaga agggccttct gtac        24

<210> SEQ ID NO 3
<211> LENGTH: 19
<212> TYPE: DNA
<213> ORGANISM: Artificial Sequence
<220> FEATURE:
<223> OTHER INFORMATION: SOX9 forward primer

<400> SEQUENCE: 3
gcatgagcga ggtgcactc        19

<210> SEQ ID NO 4
<211> LENGTH: 21
<212> TYPE: DNA
<213> ORGANISM: Artificial Sequence
<220> FEATURE:
<223> OTHER INFORMATION: SOX9 reverse primer

<400> SEQUENCE: 4
tctcgcttca ggtcagcctt g        21

<210> SEQ ID NO 5
<211> LENGTH: 20
<212> TYPE: DNA
<213> ORGANISM: Artificial Sequence
<220> FEATURE:
<223> OTHER INFORMATION: COL II forward primer

<400> SEQUENCE: 5
cgccgctgtc cttcggtgtc                                       20

<210> SEQ ID NO 6
<211> LENGTH: 21
<212> TYPE: DNA
<213> ORGANISM: Artificial Sequence
<220> FEATURE:
<223> OTHER INFORMATION: COL II reverse primer

<400> SEQUENCE: 6
agggctccgg cttccacaca t                                     21

<210> SEQ ID NO 7
<211> LENGTH: 20
<212> TYPE: DNA
<213> ORGANISM: Artificial Sequence
<220> FEATURE:
<223> OTHER INFORMATION: COL I forward primer

<400> SEQUENCE: 7
gaatgcctgg tgaacgtggt                                       20

<210> SEQ ID NO 8
<211> LENGTH: 21
<212> TYPE: DNA
<213> ORGANISM: Artificial Sequence
<220> FEATURE:
<223> OTHER INFORMATION: COL I reverse primer

<400> SEQUENCE: 8
aggagagcca tcagcacctt t                                     21

<210> SEQ ID NO 9
<211> LENGTH: 20
<212> TYPE: DNA
<213> ORGANISM: Artificial Sequence
<220> FEATURE:
<223> OTHER INFORMATION: COL X forward primer

<400> SEQUENCE: 9
tgctgccaca aatacccttt                                       20

<210> SEQ ID NO 10
<211> LENGTH: 20
<212> TYPE: DNA
<213> ORGANISM: Artificial Sequence
<220> FEATURE:
<223> OTHER INFORMATION: COL X reverse primer

<400> SEQUENCE: 10
gtcgaccagg agtaccttgc                                       20

<210> SEQ ID NO 11
<211> LENGTH: 18
<212> TYPE: DNA
<213> ORGANISM: Artificial Sequence
<220> FEATURE:

<223> OTHER INFORMATION: OCN forward primer

<400> SEQUENCE: 11
gtgacgagtt ggctgacc                                          18

<210> SEQ ID NO 12
<211> LENGTH: 19
<212> TYPE: DNA
<213> ORGANISM: Artificial Sequence
<220> FEATURE:
<223> OTHER INFORMATION: OCN reverse primer

<400> SEQUENCE: 12
tggagaggag cagaactgg                                         19

<210> SEQ ID NO 13
<211> LENGTH: 24
<212> TYPE: DNA
<213> ORGANISM: Artificial Sequence
<220> FEATURE:
<223> OTHER INFORMATION: RUNX2 forward primer

<400> SEQUENCE: 13
cttcacaaat cctcccagta gcta                                   24

<210> SEQ ID NO 14
<211> LENGTH: 26
<212> TYPE: DNA
<213> ORGANISM: Artificial Sequence
<220> FEATURE:
<223> OTHER INFORMATION: RUNX2 reverse primer

<400> SEQUENCE: 14
ggtttagagt catcaagctt ctgtct                                 26

<210> SEQ ID NO 15
<211> LENGTH: 26
<212> TYPE: DNA
<213> ORGANISM: Artificial Sequence
<220> FEATURE:
<223> OTHER INFORMATION: ACTIN forward primer

<400> SEQUENCE: 15
tgaaggtcgg agtcaacgga tttggt                                 26

<210> SEQ ID NO 16
<211> LENGTH: 24
<212> TYPE: DNA
<213> ORGANISM: Artificial Sequence
<220> FEATURE:
<223> OTHER INFORMATION: ACTIN reverse primer

<400> SEQUENCE: 16
catgtgggcc atgaggtcca ccac                                   24